US006482949B1

(12) United States Patent
Sessler et al.

(10) Patent No.: US 6,482,949 B1
(45) Date of Patent: Nov. 19, 2002

(54) COLORMETRIC SENSOR COMPOSITIONS AND METHODS

(76) Inventors: Jonathan Sessler, 5005 Crestway Dr., Austin, TX (US) 78731; Bruno Andrioletti, 44, Rue René Hamon, 94800 Villejuif (FR); Andrew Carl Try, 4/141 Croydon Road, Croydon, NSW, 2132 (AU); Christopher Black, 1214 Lacey Oak Loop, Round Rock, TX (US) 78681

( * ) Notice: Subject to any disclaimer, the term of this patent is extended or adjusted under 35 U.S.C. 154(b) by 0 days.

(21) Appl. No.: 09/579,040

(22) Filed: May 26, 2000

Related U.S. Application Data

(60) Provisional application No. 60/136,467, filed on May 28, 1999.

(51) Int. Cl.[7] ............... C07D 403/14; C07D 471/14
(52) U.S. Cl. ............... 544/343; 544/344; 544/353; 544/354; 544/355; 544/356
(58) Field of Search ............... 544/343, 344, 544/354, 355, 356, 353

(56) References Cited

PUBLICATIONS

Hawley, Gessner, "The condensed Chemical Dictonary", 1977, Van Nostrand, New York, pp. 419 and 436.*
Cram, D.J. and Hammond, G.S. "Organic Chemistry, 2nd Ed.", McGraw–Hill, New York, 1964, p. 18 and .*
John D. Roberts and Marjorie C. Caserio, "Basic Principles of Organic Chemistry", Benjamin, New York, 1964, pp. 18–19 and 966–967.*
Streitwieser, A. and Heathcock, C.H., "Introduction to Organic Chemistry, 2nd Ed.", Macmillan, New York, 1981, p. 1061.*
Fessenden, R.J. and Fessenden, J.S., "Organic Chemistry", 1982, Willard Grant Press, Boston, p. 451.*
Kurapov et al, Chemical Abstract 108:96635 for SU 1348335.*
Black et al J. Am. Chem. Soc. 121 (1999) 10438–10439.*
Gale et al. Chem. Commun. 1998, 1–8.
Bianchi, A. et al. Dietrich, B.; Hosseini, M.W. in *Supramolecular Chemistry of Anions*; Wiley–VCH: New York, 1997, pp 45–62.
Schmidtchen, F.P. *Nachr. Chem, Tech. Lab.* 1988, 36, 8–17.
K.L. Kirk *Biochemistry of the Halogens and Inorganic Halides* Plenum Press: New York, 1991, p 58.
B.L. Riggs *Bone and Mineral Research, Annual 2* Elsevier: Amsterdam, 1984, pp 366–393.
M. Kleerekoper *Endocrinol. Metab. Clinic.* North Am. 1998, 27, 441–452.
A. Wiseman *Handbook of Experimental Pharmacology* XX/2:.; Part 2, Springer–Verlag: Berlin, 1970, pp 48–97.
Sessler, J.L. et al. *Anion Advances in Supramolecular Chemistry*; Lehn, J.M., Ed; JAI Press Inc., 1997; vol. 4, pp 97–142.
Gale, P.A., et al. J. Am. Chem. Soc. 1996, 118, 5140–5141.
Sessler, J.L., et al. Chem. Eur. J. 1998, 4, 1095–1099.
Dietrich, B.; et al. J. Am. Chem. Soc. 1981, 103, 1282–1283.
Hosseini, M.W., et al. Helvetica Chimica Acta 1988,, 71, 789–756.
Dietrich, B., et al. Helvetica Chimica Acta 1979, 62, 2763–2787.
Metzger, A. et al. Chem. Int. Ed. Engl. 1997, 36, 862–865.
Oddo, B. Gazz Chim. Ital. 1911, 41, 248–255.
Behr, D.; et al. Acta Chem. Scand. 1973, 27, 2411–2414.
Sessler, J. L., et al. New J. Chem. 1992, 16, 541–544.
Cheeseman, G. W. H. 1962, J. Chem. Soc., 1170–1176.
H. Fischer; H. Orth in "*Die Chemie Des Pyrrols*," p. 381; I. Band, Ed., Akademische Verlagsgesellschaft, M.B.H., Leipzig, 1934.

* cited by examiner

*Primary Examiner*—Mukund J. Shah

(57) ABSTRACT

The present invention provides novel compounds exemplified by pyrrolic nitrogens used as anion and neutral species recognition elements with an aromatic core as a signal group. Described are methods for the synthesis of various pyrrole aryl compounds as well as various applications for these compounds. Methods of use include the binding and detection of specific analytes in a mixture and, in some examples, the separation of the analyte from the mixture. Additional methods of use include the transport of therapeutic agents and the sensing of components, degradants, and impurities in foodstuffs.

22 Claims, 2 Drawing Sheets

COLORMETRIC SENSOR COMPOSITIONS AND METHODS

This application claims priority to U.S. Provisional Application No. 60/136,467 filed May 28, 1999.

The government owns rights in the present invention pursuant to National Institutes of Health (grant no. GM 58907 to Jonathon L. Sessler), the National Science Foundation (CHE-9725399 to Jonathan L. Sessler), the Texas ARP (grant 003658-102 to JLS) and a NIH Postdoctoral Fellowship to Christopher B. Black.

BACKGROUND OF THE INVENTION

1. Field of the Invention

The invention relates generally to compositions and methods for binding and optically sensing anions, cations, and neutral species. Analytical methods for such species is the primary goal of optical sensing. These methods may be qualitative or quantitative. In particular, compositions containing pyrroles as the key recognition element and a quinoxaline backbone as part of the compound, are shown to provide a system with a built-in optical probe for selective sensing.

2. Description of Related Art

In the recent decades, supramolecular chemists have devoted considerable effort to developing systems capable of recognizing, sensing, and transporting anions (Dietrich, et al., 1997). This is an area of effort that is considered both timely and important. Indeed, some 70 to 75% of all natural biological processes are thought to involve a negatively charged species (Schmidtchen, 1988).

Anion recognition constitutes an important problem area within the generalized field of supramolecular chemistry. Not surprisingly, therefore, it has been pursued extensively, particularly within the calixarene domain. Indeed, most attention has focused on calixarene systems that have been modified, via attachment to, or reaction with, electron deficient metal centers, so as to make more electrophilic the normally $\pi$-electron rich calixarene moiety.

Anions constitute key components in food stuffs (e.g., fluoride, citrate and benzoate) and are products for, and pollutants from, modern agriculture (e.g., phosphate and nitrate) and can also act as potent toxins (e.g. cyanide). One anion, pertechnetate, is critical to radio-diagnostic and therapy procedures and, in a different isotopic form, is a major radioactive pollutant. Given these few examples, it is clearly important that we have a means to readily monitor the presence of these species in our everyday environment.

Among the range of biologically important anions, fluoride is of particular interest due to its established role in preventing dental caries (Kirk, 1991). Fluoride anion is also being explored extensively as a treatment for osteoporosis, (Riggs, 1984 and Kleerekoper, 1998) and, on a less salubrious level, can lead to fluorosis, (Wiseman, 1970 and Gale, et al., 1996) a type of fluoride toxicity that generally manifests itself clinically in terms of increasing bone density. This diversity of function, both beneficial and otherwise, makes the problem of fluoride anion detection one of considerable current interest. Thus, while traditional methods of fluoride anion analysis, involving, e.g., ion selective electrodes and $^{19}$F-NMR spectroscopy remain important, there is an increasing incentive to find alternative means of analysis, including those based on the use of specific chemosensors. Particularly useful would be systems that can recognize fluoride anion in solution and signal its presence via an easy-to-detect optical signature.

In the past few years, a wide range of anion sensors have been proposed (sapphyrins, Sessler, et al. 1997; calixpyrroles, Gale, et al. 1996 and Sessler, et al., 1998; cyclic polyamines, Dietrich, et al., 1981; Hoseini and Lehn, 1988) guanidinium (Dietrich, et al., 1981 and Metzger, et al., 1997)) that present varying degrees of affinity (and selectivity) toward anions such as $F^-$, $Cl^-$, $H_2PO_4^-$ and/or carboxylates. Unfortunately, and in spite of considerable effort, a need for good anion sensors remains. The number of anion sensors which can select for one biological anion over a range of anions present in vivo (phosphate, chloride, fluoride, etc.) remains at best, very limited. While there exists small molecule sensors which can bind anions relatively well, they do so with little or no specificity. This is particularly true in the case of fluoride anion where few, if any, easy-to-use signaling agents exist.

In addition to anion sensing, it is also desirable to develop sensing elements capable of sensing cations and neutral species. The presence or absence, as well as the level of, various neutral molecular species is a useful diagnostic tool that can signal chemical decomposition. One example is the sensing of cis-3-hexenal (or chemical derivatives thereof), a metabolite of the bacterial *E. Coli*, Salmonela, and Lysteria. Such sensors would find applicability in the food industry as detectors of food contamination and spoilage. They could, for instance, be incorporated into food packaging materials.

Therefore, a need exists to develop methods and compositions for the selective detection of anions, cations, and neutral species in general, and for fluoride in particular. A motivation for the preparation of new sensors is to obtain sensor compounds designed to recognize selectively a particular analyte within a range of species and produce an easily detected signal.

SUMMARY OF THE INVENTION

The present invention provides novel compounds containing both pyrrole-derived anion and neutral species recognition subunits and an aromatic core as the optical or visual signaling group to provide chemosensors that allow for the convenient, color-based sensing of anions. Most commonly, the aromatic core will be a quinoxaline moiety, but may be any aryl system having two pyrroles covalently bound to neighboring (but not necessarily directly ajacent) carbons on an aryl moiety through a C—C single bond connecting pyrroles and the aromatic moiety.

Formula I illustrates the general pyrrole-aryl systems ($\alpha,\alpha$ and $\beta,\beta$ substitution on the pyrrole rings) along with the specific pyrrole-quinoxaline analog shown directly below. Note that the pyrrole substitution may also be mixed, i.e, $\alpha,\beta$ or $\beta,\alpha$. As used herein, "aryl" means any aromatic system consisting of one or more rings which may be homonuclear or heteronuclear, and which may or may not contain aromatic or non-aromatic side groups (substitution), and which may be further complexed to one or more metals. The present invention further provides methods of use and synthetic schemes for these novel compounds.

Formula I

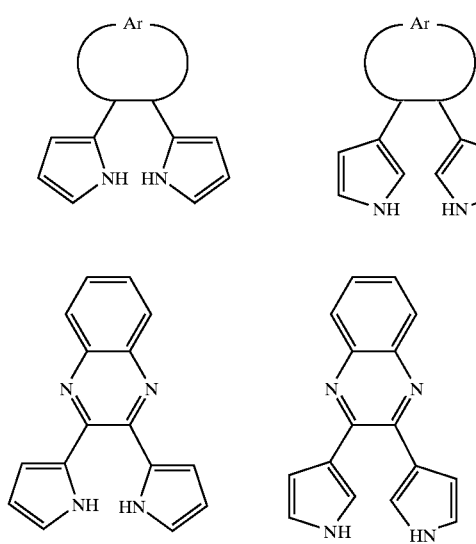

Ar = Aryl

The present invention provides novel compounds exemplified by the pyrrolic nitrogens used as anion recognition elements with an aromatic core as a signal group. The compounds of the present invention are termed pyrrole-aryls, and as used herein, the compounds of the present invention which, at least, combine these two elements will be referred to as such. Although not shown above, the pyrrole carbon atoms may also be substituted. The aryls may or may not contain heteroatoms. Subsituents may include, but are not limited to, hydrogen, alkyl, hydroxyalkyl, glycol, polyglycol, amino, nitro, halo, cyano, aryl, heteroaryl, thio, thioalkyl, amide, ester, acyl, or carboxy and may be the same or different at each occurrence.

Compounds of the present invention may be prepared by a condensation between a 1,2-diamine and a 2,3-dipyrryl ethanedione as shown in Scheme 1.

Scheme 1

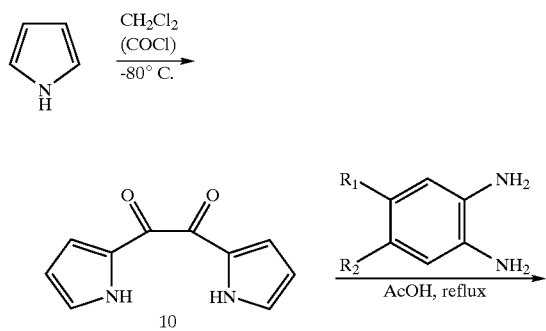

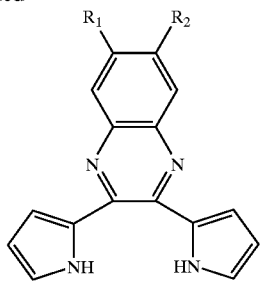

1: $R_1 = R_2 = H$
2: $R_1 = R_2 = OCH_3$
3: $R_1 = R_2 = NO_2$
4. $R_1 = R_2 = CH_3$
5: $R_1 = R_2 = O(CH_2CH_2O)_nCH_3$
6: $R_1 = R_2 = O(CH_2)_nCH_3$
7: $R_1 = H, R_2 = NO_2$
8: $R_1 = NH_2, R_2 = NO_2$
9: $R_1 = NH_2, R_2 = NH_2$
$n = 1-10$

While specific substituents are listed above, the quinoxaline analogs may have a wider variability of substituent groups. $R_1$ and $R_2$ may be, individually at each occurrence, hydrogen, alkyl, hydroxyalkyl, glycol, polyglycol, amino, nitro, halo, cyano, aryl, heteroaryl, thio, thioalkyl, amide, ester, acyl, or carboxy. Although not shown above, any or all of these possible substitutions may be present on the remaining available carbon atoms of the quinoxaline. Additionally, any or all of these same possible substitution combinations may also be present on the α or β positions, or on both the α and β positions (relative to nitrogen) of the pyrrole rings.

Oxalyl chloride, o-phenylenediamine, 4-nitro-1,2-diaminobenzene were purchased from Aldrich and used without further purification. 4,5-Diamino-1,2-dimethoxybenzene was prepared according to the method of Sessler, 1992. 4,5-Dinitro-1,2-diaminobenzene was prepared according to the method of Cheeseman, 1962.

Thus, in a second respect, the present invention is the 2,3-dipyrryl-ethanediones used to produce the pyrrole-aryls. In this aspect of the invention the dipyrryl-ethanediones are of Formula II:

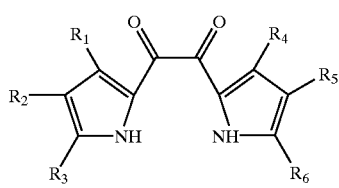

wherein individually at each occurrence, each of $R_1$–$R_6$ are the same or different and are hydrogen, alkyl, hydroxyalkyl, glycol, polyglycol, amino, nitro, halo, cyano, aryl, heteroaryl, thio, thioalkyl, amide, ester, acyl, or carboxy. Though not shown the di-β-linked diketone (bridging group attached to pyrroles in position β to nitrogen atoms) is within this family, as is the mixed α, β-linked diketone.

These dipyrryl-ethanediones may be produced by reaction of a pyrrol either commercially available or obtainable through synthetic methods known to one of skill in the art, with oxalyl chloride as represented in Scheme 1 to generate a variety of dipyrryl-ethanediones.

Further to this, the present invention provides a new set of novel dione compounds generated from the reaction of bipyrroles, terpyrroles etc. with oxalyl chloride to generate the compounds of Formula III:

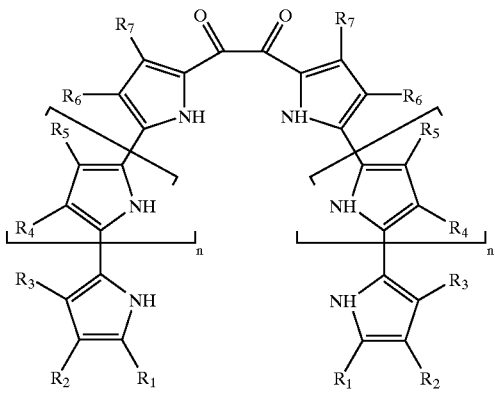

wherein individually at each occurrence, each of $R_1$–$R_7$ are the same or different and are hydrogen, alkyl, hydroxyalkyl, glycol, polyglycol, amino, nitro, halo, cyano, aryl, heteroaryl, thio, thioalkyl, amide, ester, acyl, or carboxy and n=0–10. The analogous $R_x$ groups on either side of the diketone bond may be the same or different (i.e., $R_1$, $R_2$, . . . $R_x$ on one side of the diketone bond may be the same or different from the corresponding $R_1$, $R_2$, . . . $R_x$ on the opposite side, etc.; additionally, the $R_4$ and $R_5$ groups may have variability amongst individual pyrrole subunits; e.g. $R_4$ on any given subunit may be the same or different from a corresponding $R_4$ on any other subunit). Symmetry in substitution along the axis bisecting the diketone bond or among any pyrrole subunit is not required and maximum variability in substitution is possible so long as the general formula is followed.

These novel diones may then be used to generate novel pyrrole-aryl compounds such as 2,3-di(bipyrryl) quinoxalines (n=0), 2,3-di(terpyrrylquinoxalines (n=1), 2,3-di(tetrapyrrylquinoxaline (n=2) etc. The preferred route is via a condensation reaction involving the two ketones with an aryl compound.

It is further contemplated that the 2,3-dipyrryl-ethanediones may undergo reaction with any 1,2-diamine under conditions outlined in Scheme 1 to generate a variety of new compounds for anion sensing as represented by Formula IV (functionalized quinoxaline analogs) and Formula V (functionalized pyrrole, functionalized quinoxaline analogs), respectively.

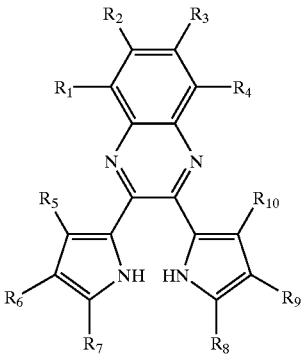

Formula IV

Formula V

In Formula IV and V, respectively, individually at each occurrence, each of $R_1$–$R_4$ and $R_1$–$R_{10}$ are the same or different and are hyrdogen, alkyl, hydroxyalkyl, glycol, polyglycol, amino, nitro, halo, cyano, aryl, heteroaryl, thio, thioalkyl, amide, ester, acyl or carboxy. Note that the quinoxaline analogs are used for illustrative purposes in the above examples. It is readily apparent to one of ordinary skill in the art that an appropriate aryl or substituted aryl may be used in place of quinoxaline for the more generalized pyrrole-aryl compounds. As earlier discussed, the only requirement is orbital overlap of the ring systems comprising the aryl and pyrrole groups which are altered by bond rotation upon binding of substrate (anion, cation, or neutral atom or molecule):

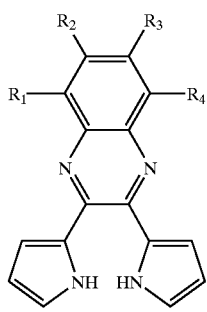

Ar = Aryl
S = Substrate

The pyrrole groups are preferably on, but need not be on, adjacent carbons of the aryl moiety. Note that the nitrogen atoms may be deprotonated to afford cation-binding systems.

2,3-dipyrrol-2'yl-5,6-dicyanopyrazine (Example 30) is an example of an analogous pyrrole-aryl sensing compound that does not contain the quinoxaline moiety. The present invention provides a solution to the needs described herein above by producing compounds and methods for selective sensing. In particular, the preferred pyrrole-aryl compounds of the present invention have the ability to selectively bind fluoride anion over biologically important competitors such as chloride and phosphate and in doing so, produce a color change from yellow to orange in the case of 1 and from orange to purple for 3 and 8 which is, in some circumstances, visible to the naked-eye. It was further found that for these particular analogues, organic solvents encourage fluoride binding while polar solvents, such as methanol or water, lead to fluoride dissociation. This property would allow for the original sensor to be regenerated by changing solvents once the sensing is complete.

The compounds of the present invention are particularly contemplated for use in fluoride sensing, especially in the presence of other biologically common anion species. While analogues such as 3 may display other anion sensitivities, the ability to selectively sense fluoride anion would be particularly useful for many purposes as further discussed in Examples 40 and 42.

Therefore, an aspect of the present invention is the development of analytical methods for species which are selectively bound by the pyrrole-aryl compounds. As used herein, "analysis" means both quantitative and qualitative analysis. As used herein, optical methods included instrumental spectroscopic methods as well as visual observation. While the focus is on optical and visual analytical methods, electrochemical methods employing the pyrrole-aryls as sensing elements are also envisioned. Time-based analytical methods, such as those monitoring changes in fluorescence lifetimes (as well as other photophysical temporal phenomena) measurements are also envisioned. Either of these analytical examples would be sensitive to the modification of the molecular electronic structure of the sensing compound which would be caused upon substrate binding. Many other analytical measurements sensitive to such changes in electronic structure and which are known to those of skill in the art would be applicable in the present invention.

It is contemplated that the pyrrole-aryls of the present invention have a wide variety of uses. A range of compounds with a large number of substituents fall within the scope of the present invention. The precursor molecules, the starting pyrrole or dione, may be derivatized as desired or the pyrrole-aryl may be modified post synthetically to yield compounds with desired substituents. Therefore, it is contemplated that the selectivity of the pyrrole-aryl compounds of the present invention will have a number of different selectivities achieved by variation of substituents within the structure.

It is also envisioned that the binding and sensing capabilities of the pyrrole-aryls can be further exploited by surface immobilization. Functionalization of the pyrrole-aryl with reactive groups would afford the ability to attach them to solid phases. Polymer phases, silica and polystyrene, among others, are solid surfaces which find applicability in this embodiment of the invention. Surface immobilization is useful in the separation sciences, in the fabrication of sensors such as fiber optic probes, as well as other applications. In the field of separation science, surface immobilization can be used to fabricate novel stationary phases. In fiber optic sensing application, immobilization of the sensing element on the distal end of a fiber optic tip can be used to construct sensors useful for remote analyses. Fiber optic sensors are known to be amenable to remote sensing, such as in vivo, in vitro or in-situ sensing. In vivo applications would involve miniaturization of the fiber optic tip, thus the high sensitivity achievable with the pyrrole-aryls is particularly advantageous. In the area of foodstuff analysis, surface immobilization of the pyrrole-aryls onto fiber optic sensors, or alternatively, onto packaging components of foodstuffs is envisioned to afford a quick, convenient way to monitor spoilage.

Additionally, the pyrrole-aryls of the present invention may be modified to increase aqueous solubility for use analytically or as therapeutic agents. In sensing applications, modification of solubility may be used to optimize a sensing element for the particular environment to be interrogated. This is performed through functionalization of the pyrrole-aryl compounds with groups that impart water solubility. Polar groups, especially those which readily carry a charge under various conditions, are candidates for such functionalization. Carboxy, hydroxy, and amine groups are most obvious but others are possible. Enhancing water solubility is useful therapeutically by enhancing bioavailability.

Additional modifications are envisioned in which the pyrrole-aryls may be incorporated into macrocyclic compound. Porphyrin-type complexes are but one example further described below. By incorporating the binding site into a macrocyclic compound, novel compounds may be made to optimize transport of therapeutic agents, or to tailor the sensing element for a specific application. Metal-linked systems of pyrrole-aryls are another aspect of the present invention. These may be prepared by first preparing silyl derivatives having, for example, TMS groups appended. Subsequent deprotection and reaction with a metal salt will afford metal linked systems.

Therapeutic uses of the compounds of the invention are also described. The binding capabilities may be exploited for uses as transporting agents. Anionic, cationic, and neutral species, through binding to the appropriate pyrrole-aryl, can be directed in vivo to areas where their therapeutic effect is optimally realized. The high affinity for a number of these species for chloride ion has potential applicability in the treatment of cystic fibrosis. Cystic fibrosis is characterized by a reduced ability to effect chloride ion transport at the cellular level involves the localized introduction of chloride ion. A means for enhancing the transport of chloride ion is therefore useful in such treatments. While this is one specific example, the ability to transport therapeutically active agents is expected to have wider applicability. This has the beneficial advantages of allowing for more efficient and lower dosages, which minimizes side and toxicity effects.

The compounds of the present invention provide a further advantage in the ease with which the pyrrole-aryls can, in light of the present disclosure, be modified. The synthetic steps are relatively simple and inexpensive to carry out. As the optical and binding properties can be controlled by the types of substituents present, this allows enough flexibility to accommodate a number of applications as well as the fine tuning of desired properties, for application in a specific environment.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
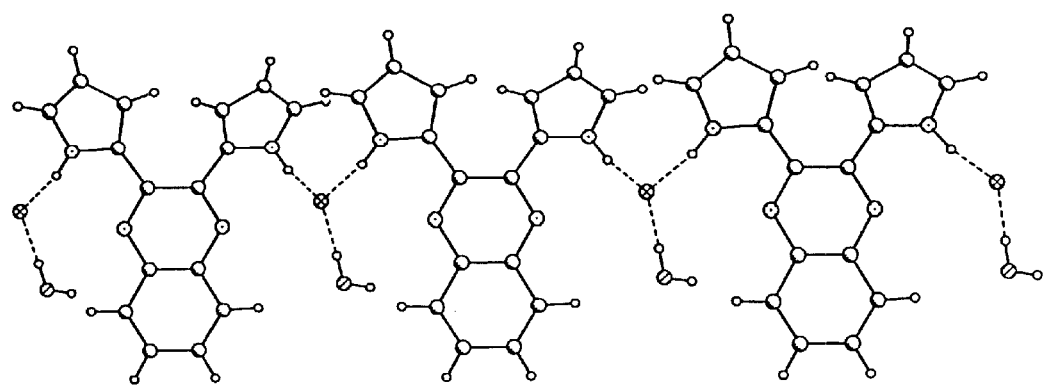
FIG. 1 provides a view of the hydrogen bonded complex of [1.F]$^-$ as it extends along the a axis. Hydrogen bonding interactions are indicated by dashed lines. The relevant geometry for these interactions are: N1—H1N . . . F1 (related by x−1, y, z), N . . . F 2.629(2) Å, H . . . F 1.63(3) Å, N—H . . . F 169(2)°; N17—H17 . . . F1, N . . . F 2.640(2) Å, H . . . F 1.69(3) Å, N—H . . . F 168(2)°; O1w—H1w . . . F1, O . . . F 2.590(2) Å, H . . . F 1.70(3) Å, N—H . . . O 177(3)°.

The present invention generally relates to methods and compositions for anion and neutral species binding, analysis and recognition. As used herein, "analysis" encompasses both quantitative or qualitative analysis. In particular, the compounds and methods of the present invention utilize pyrroles as the key recognition-inducing component and aryl groups as optical reporting group. Many of the disclosed compounds contain quinoxalines as the aryl as part of the backbone structure to provide systems with built in chromophores and/or fluorophores for optical sensing. While quinoxaline is preferred, the invention is not limited to sensing compounds with this aryl component.

With reference to the substituents contemplated for use in accordance with the present invention, alkyl may be of the repeating unit —$(CH_2)_nCH_3$. The number of repeating units within an alkyl substituent may be up to fifty, preferably up to 20 and more preferably from 0–10. Representative examples of alkanes include methane, ethane, straight chain branched or cyclic isomers of propane, butane pentane hexane, octane, nonane and decane. Representative examples of substituted alkyls include alkyls substituted by two or more functional groups as described herein. Hydroxyalkyls includes alcohols of alkyl groups as defined previously. Representative examples of hydroxyalkyls include alcohols of methane, ethane, straight chain branched or cyclic isomers of propane, butane, pentane hexane, octane, nonane and decane. Hydroxyalkyl is meant to include glycols and polyglycols. Representative examples of glycols include diols of ethane, straight-chain, branched or cyclic isomers of propane, butane, pentane hexane, octane, nonane and decane. Representative examples of polyglycols include polyethylene glycol, polypropylene glycol, polypropylene diol and polybutylene diol. Representative examples of oxyalkyls include the alkyl groups defined herein above having ether linkages.

Representative examples of thioalkyls include thiols of an alkyl as described herein above including thiols of ethane, thiols of straight-chain, branched or cyclic isomers of propane, butane, pentane, hexane, heptane, octane, nonane and decane. Sulfate substituted alkyls include alkyls as described above substituted by one or more sulfate groups, a representative example of which is diethyl sulfate (($C_2H_5$)$_2SO_4$); they also include simple anionic sulfate or sulfonate substituents such as —$C_2H_5SO_3^-$.

As used herein, aryl refers to a compound whose molecules having either the pi-conjugated ring of benzene or the condensed rings of the other aromatic derivatives including heteroatom-containing aromatic derivatives (heteroaryls). They may additionally contain non-aromatic subsituents as side groups or be linked to metals. Representative examples include benzene, naphthalene, phenanthrene, phenanthroline, and anthracene. A heteroaryl compound, as used herein, refers to a compound which contains more than one kind of atom in an aromatic ring. Representative examples include pyridine, pyrimidine, furan, thiophene, pyrrole and imidazole.

Representative examples of amines include primary, secondary and tertiary amines of an alkyl as described herein above.

Representative examples of carboxy groups include carboxylic acids of the alkyls described above as well as aryl carboxylic acids such as benzoic acid. Carboxy groups also include derivatives of carboxylic acids such as esters, amides, acyl halides, anhydides, and nitriles. Representative examples of carboxyamides include primary carboxyamides (RCONH$_2$), secondary (RCONHR) and tertiary (RCONR'R") carboxyamides where each of R' and R" is a functional group as described herein and the carboxy group is as defined herein above.

Representative examples of ester groups include compounds of the form RCOR' where the R group is an alkyl as described herein above and where R' is a functional group as described herein. Representative examples of acyl groups include acyl derivatives RCO— or ArCO—, wherein R is an alkyl as described herein above and Ar is an aryl group as defined herein.

The choice of metal ion for complexing to analogues of the present invention will generally be dependent on the use or intended use of the analogue. For example, representative metals for the porphyrin derivative include Zn, Cu, Pd, Ni, Fe, Co, Ru, Rh, and Os.

In one embodiment a method for anion sensing is disclosed using compounds of general Formula I shown herein above. Importantly, the general structures may possess substituent (R) groups at any carbon capable of accommodating such substituents (i.e., those bound to at least one hydrogen atom in the general structures) each R being defined as above.

The synthesis of compounds represented in Formula I is outlined in Scheme 1. In this embodiment the substituents $R_1$ and $R_2$ are introduced during the synthesis on the aryl 1,2-diamine as shown. It would be well appreciated by one of skill in the art, in light of the present disclosure, that a wide variety of aryl 1,2-diamines may be condensed with a 1,2-dipyrryl ethanedione to provide a vast array of different compounds and that any or all of the remaining positions on the 1,2-diamine may bear substituents as exemplified by Formula IV.

Additionally, compounds derived from those represented by Formula I are contemplated for the formation of metal complexes. For example, structure 9 may be condensed with 1,10-phenanthroline-5,6-dione to form compound 13. An alternate condensation of structure 9 with 5,6-diamino-1,10-phenanthroline affords structure 14. Both of these examples are shown in Example 34 where the metal binds through the phenanthroline nitrogens. Furthermore, compounds with altered fluorescence, represented by 15 and 16, may be synthesized using conditions similar to those provided in Example 34. Additionally, those syntheses detailed in other Examples could be effected using the appropriate dione.

Further variants may be produced by using a porphyrin dione in the condensation to form a compound exemplified by structure 17 (Example 34), bearing a range of substituents at the meso and β-pyrrolic positions. The porphyrin may be metallated using standard techniques to generate a range of compounds containing various metals (for example Zn, Cu, Pd, Ni, Fe, Co, Ru, Rh, Os). For the substituents shown in structure 17, individually at each occurrence, each of $R_1$, $R_4$, $R_7$, $R_{10}$, is a hydrogen atom, alkyl, aryl or heteroaryl and individually at each occurrence, each of $R_2$, $R_3$, $R_5$, $R_6$, $R_8$, $R_9$ is a hydrogen atom, alkyl, aryl or heteroaryl, halo, cyano, acyl, carboxyl, carboxy ester, carboxyamide, nitro or amino. While these are the preferred substituents, a wider range of substitution is possible and may even be desirable for given applications. One of skill in the art can appreciate the wide range of substitution possible. These porphyrin containing compounds are contemplated for analytical applications, particularly as redox-based and/or optical sensors.

Other possible metal-containing analogs include pyrrole-aryl tethered metallocenes such as ferrocene. Additionally, crown ether-derivatized pyrrole-aryls can be used as metal bearing agents. Other host-guest species such as cyclodextrins may be coupled covalently to the pyrrole-aryls. Metallocenes, crown-ethers, and cyclodextrins act as substrate binders and catalysts in their own distinctive chemistries. Binding to the pyrrole-aryls will produce novel, synergistic binding effects. These are expected to further extend the usefulness of these novel species to electrochemical applications, particularly for analytical sensing. It is envisioned that the metal-complexed derivatives will be useful as ion channels. The selective binding and transport capabilities of such "pore-forming" species will have application as transport agents therapeutically and as sensors analytically.

The dipyrrole quinoxalines of the present invention may also be modified post-synthetically to introduce a variety of substituents at the α and/or β pyrrolic positions, $R_3$ and $R_4$, as shown in compound 18 (Example 35). The substituents $R_1$ and $R_2$ are as previously described, $R_3$ and $R_4$ may be the same or different, and may be halides, including, iodo and bromo, alkyl, aryl, heteroaryl, acyl, nitrile, carboxy amide, carboxy ester or sulfide. The introduction of these substituents allows for further modification of properties for a given compound. Using protocols well known in the art, the dibromo or diiodo compounds may be used to generate a further range of a substituted compounds such as those provided by structure 19. Compounds such as 20, may be used in subsequent reaction with a metal salt, such as $[PdCl_2(PEt_3)_2]$, {i.e., bis(triethylphosphine)palladium(II) dichloride, or phosphino-platinum dichloride complexes, following removal of the TMS groups to afford metal linked systems.

The pyrroles used in accordance with the present invention to prepare the pyrryl-quinoxalines, may be derivatized as represented in Scheme 5, structure 21 (Example 36). The pyrrole units with $R_1$—$R_3$ substituents may, in some cases, be commercially available or in other instances may be prepared through synthetic methods well known to one of skill in the art.

The 1,2-dipyrryl-ethanediones used in the present invention may be generated using the above-described pyrroles in a reaction with oxalyl chloride to provide many different 1,2 dipyrryl-ethanediones as shown in Scheme 5. Substituents $R_1$, $R_2$ and $R_3$ are alkyls, hydroxyalkyls, substituted alkyls, amines, halo, cyano, aryl, heteroaryl, thio, thioalkyl, amide, ester, acyl and carboxy. Representative examples include those described previously with the preferred substituents as listed in Example 36 for compound 22.

Additionally, several other compounds are contemplated for use in the reaction with oxalyl chloride to generate a series of diones. In particular, many different polypyrroles, bipyrroles (n=0), terpyrroles (n=1), up to and including n=10 may be employed as shown in Scheme 6 (Example 36) to generate compounds exemplified by structure 24. $R_1$ through $R_7$ are alkyl, hydroxyalkyl, glycol, polyglycol, amino, nitro, aryl, heteroaryl, acyl, halo, carboxy ester, carboxy amide and carboxy as previously described, such that $R_1$—$R_7$ may be the same or different at each occurrence and n is 0–10, with $R_1$ through $R_7$ as H and n=0 being preferred.

It is further contemplated that quinoxaline compounds of the present invention with a free α-position may undergo further reaction as shown in Schemes 7A–7D (Example 37) for incorporation into macrocycles for use as sensing/transporting agents, and optical display devices. A wide variety of conditions known to one of skill in the art, may be employed to promote reaction of the remaining α-free position on the pyrrole rings as shown in Example 37. These compounds are as represented by structures 25–32, and thus fall within the scope of the present invention.

Further sources of synthetic variation may be generated using diones comprised of various heterocyclic rings as shown in Example 38. These compounds may provide alternate selectivity for a variety of other analytes, such as metal ions in the case of the furan, thiophene, pyridine and pyridine N-oxide derived systems.

Another source of variation involves the use of dianions of either the 1,2-di-pyrrylethanedione or the 2,3-di-pyrrylquinoxalines, as represented in Example 39, in accordance with the present invention. These dianions are contemplated for use as ligands for the generation of metal complexes. Such compounds would find use in the areas of molecular wires and display devices.

It is particularly contemplated that the pyrrole quinoxaline compounds of the present invention will be of use as anion sensors. Example 40 provides a further discussion. It is further contemplated that the preferred compounds will find utility as novel fluoride anion sensors and receptors, and other examples wil find use as chloride and phosphate sensors and receptors. The unsubstituted pyrrolic nitrogens provide anion binding sites as detailed in Examples 31–33. Furthermore, the pyrrole quinoxaline compounds of the present invention provide a quinoxaline core as a chromophoric signal group for the color-based sensing of anions.

Any one of a wide variety of anions may be detected using the pyrrole-aryls or alternate heterocyclic quinoxalines in accordance herewith. These anions include, but are not limited to, cyanide anion, phenolate anion, carboxylate anion, sulfate anion, sulfonate anion, nitrate anion, nitrite anion, bromide anion, pertechnetate anion, perrhenate anion, chloride anion, phosphates and phosphonates.

Additionally, the disclosed methods are contemplated for binding or complexing a range of analytes, including anion, cations and neutral species, but particularly anions and neutrals. Therefore, also contemplated are phosphate-containing compounds, including simple alkyl or aryl phosphates, alkyl phosphonates, nucleotides, oligo- and polynucleotides such as DNA, RNA and anti-sense constructs and nucleotide analogues. Representative examples of phosphates include phosphate or polyphosphate groups. Representative examples of phosphate substituted alkyls include alkyls as described above substituted by one or more phosphate or polyphosphate groups. Representative examples of phosphonate substituted alkyls include alkyls as described above substituted by one or more phosphonate groups.

The term nucleotide, as used herein, refers generally to any moiety that includes within its structure a purine, pyrimidine, or nucleic acid with a ribose group and at least one phosphate group, or any derivative of these such as a protected nucleotide. Thus the term nucleotide includes adenosine tri-, di- and monophosphate, guanosine tri-, di- and monophosphate, cytidine tri-, di- and monophosphate, thymidine tri-, di- and monophosphate, uridine tri-, di- and monophosphate and xylo-guanosine monophosphate a well as any nucleotide derivative based upon these or related structures.

As discussed previously, the increased specificity and optical analysis makes this class of anion sensors considerably more effective at anion recognition and detection than other classes of molecules. The capacity of pyrrole-aryls and analogues thereof, to effect specific sensing of anions in general, and fluoride in particular, is contemplated to be advantageous for use in vitro and in vivo. For example, the disclosed compounds may be used to effect the construction of electrodes (analogous to pH sensing) or to fiber optic cables for analysis of drinking water, in vitro, or for in vivo fluoride sensing in the analysis of bone density. In addition to optical sensors, other applications are contemplated such as chromatography. Here for example, compounds 1–3 are coupled to a solid support. The pyrryl-quinoxalines can be attached to solid supports, via condensation reaction between complementary functional groups on the quinoxaline and the solid support, e.g., amine on quinoxaline with carboxyl on solid support to yield an amide linkage, or a carboxyl group on the quinoxaline with an amine or hydroxyl on the solid support to give an amide or ester linkage respectively. These coupled compounds may be used to separate various anions from each other and from other species in the mixture.

Additionally, the binding and/or sensing of fluorinated compounds is also contemplated. It is well established that fluorinated hydrocarbons are damaging to the atmosphere, as well as to humans, and that fluorinated phosphates are extremely toxic when ingested, for instance from chemical weapons. In order to increase solubility in aqueous solutions, derivatives containing additional pyrroles in the pyrrole-aryl system as outlined in Example 41. This would allow for analysis of fluoride levels in blood samples as well as a treatment for any detected fluorosis.

In the detection of fluoride anion as described in Examples 31–33, the preferred solvent is an aprotic one with dichloromethane particularly preferred. However, other solvents are contemplated for the appropriate analogues as described previously.

Immobilization on Solid Supports

The target pyrrole-aryl sensing compound can be covalently attached to a solid support using any of the number of methods commonly employed in the art to immobilize molecular species to solid supports. Covalent attachment of the sensing compound to the solid support may occur by reaction between a reactive site or a binding moiety on the solid support and a reactive site or another binding moiety attached to the sensing compound or via intervening linkers or spacer molecules, where the two binding moieties can react to form a covalent bond. For example, binding of a sensing compound to a solid support can be carried out by reacting a free amino group of an amino-functionalized sensing compound with a reactive carboxy of the solid support. Similarly the reaction of alcohol groups and the derivatized and native SiOH groups of silica can afford immobilization.

Coupling of a sensing compound to a solid support in this way may be carried out through a variety of covalent attachment functional groups. Any suitable functional group may be used to attach the sensing compound to the solid support, including but not limited to disulfide, carbamate, hydrazone, ester, N-functionalized thiourea, functionalized maleimide, mercuric-sulfide, gold-sulfide, amide, thiolester, azo, ether and amino. The solid support for use in separation science or sensor technologies may be made from a wide variety of materials, such as silica, cellulose, nitrocellulose, nylon membranes, controlled-pore glass beads, acrylamide gels, polystyrene, activated dextran, agarose, polyethylene, functionalized plastics, glass, silicon, brominated Wang resin, Merrifield resin, agarobiose, carboxypolystyrene HL, and TG-amino resin. Some solid support materials may require functionalization prior to attachment of the sensing compound. Solid supports that may require such surface modification include aluminum, steel, iron, copper, nickel, gold, silicon, and nonfunctionalized polymers. In the area of sensing of components, degradants, and impurities in foodstuffs, solid support materials include polyethylenes such as LDPE and ULLDPE, EVA and others. In addition to solid surface immobilization through covalent interactions, noncovalent interactions (such as that of biotin with streptavidin, for example), as well as other similar chemistries that are well-known known to those of skill in the art are applicable in the present invention. Example 43 describes the ability of a surface bound sensing compound to detect fluoride ion.

While the above examples recite solid support immobilization via covalent interactions, binding moieties may also include functional groups that attach to the solid support via a high-affinity, noncovalent interaction (such as biotin with streptavidin), as well as other means that are well-known to those of skill in the art.

The selective binding capabilities of the sensing elements described herein may be useful in a number of applications wherein it will be advantageous to have such binding on a solid support. For example, binding to silica-based supports would have utility in the separation sciences. These have additional utility in the area of fiber optic sensing. Functionalization of the sensing element with silyl alcohols groups, among others, will allows for attachment onto silica. Additionally, it will be beneficial for similar purposes to incorporate such sensing elements onto a polymer support. The molecule shown at right in the example below may be incorporated into a polymerizing chemistry known to one of skill in the art to afford a material that has the ability to behave as a sponge toward analytes of interest.

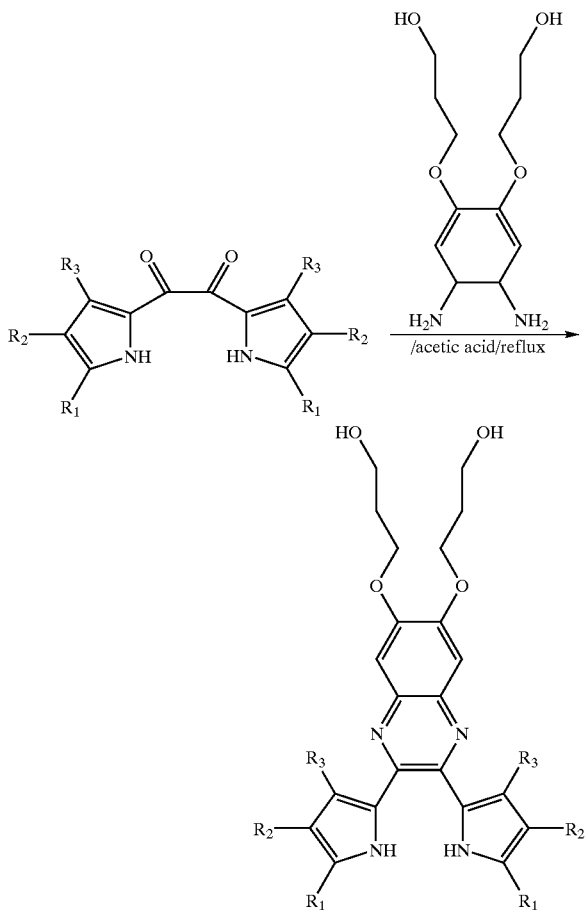

In the above example, $R_1$—$R_3$ is hydrogen, alkyl, hydroxyalkyl, glycol, polyglycol, amino, nitro, halo, cyano, aryl, heteroaryl, thio, thioalkyl, amide, ester, acyl, aldehyde, or carboxy.

Enhancement of Water Solubility

The unsubstituted pyrrole-aryls have relatively low solubility. In order to enhance further the general utility of these species as sensing compounds, it is desirable to afford one the capability of readily enhancing water solubility. Such solubility characteristics may be tailored through functionalization. Water solubility is most markedly enhanced through the functionalization of these sensing compounds with groups that readily carry a formal charge in aqueous solutions. Additionally, groups of varying polarity may be used to modify water solubility. Combinations of these groups can be used depending upon the level of water solubility sought to be imparted to the sensing compound.

Functional groups which find applicability in this regard include carboxy, amino, sulfonate, alcohols. Oxyhydroxyalkyl and oxycarboxy groups such a hydroxypropoxy and carboxyethoxy are useful in this regard. Multiply carboxylated derivatives may be used in their native form or they may be converted to ester or amide products that can be used to further append hydroxylated substituents. Polyether-linked polyhydroxylated alkyl groups, polyethylene glycols and other multi-hydroxy containing groups will also afford enhanced water solubility while allowing the sensing element to retain lipophilicity.

Pharmaceutical Compositions and Routes of Administration

Apart from the application of the subject sensing elements as in vivo and in vitro sensors, it is envisioned that they may be used as therapeutic agents. They are particularly useful in applications were anion and neutral molecule transport are necessary. One specific example involves the use of chloride ion transport for the treatment of cystic fibrosis. Cystic fibrosis is a hereditary disease characterized by the production of defective chloride channel proteins in epithelial cells, particularly the lungs. Established treatments target the symptoms of the disease but do not compensate for the poor chloride ion transport. An effective, biocompatible carrier that functions in vivo to augment cell permeability for chloride anion could provide a conceptually simple, potentially new approach to cystic fibrosis treatment. These sensing elements have therapeutic uses in any situation wherein the selective transport of an anion or neutral species is desired. One variation on the class of compounds described herein involves the derivatization with crown ethers. Such compounds would enhance the role of ion or neutral species transport.

Where clinical application of controlled release compositions is undertaken, it will be necessary to prepare the composition as a pharmaceutical composition appropriate for the intended application. Generally, this will entail preparing a sterile, physiologically compatible pharmaceutical composition that is essentially free of pathogens, as well as any other impurities that could be harmful to humans or animals. One also will generally desire to employ appropriate buffers to render the complex stable and allow for uptake by target cells.

Aqueous compositions of the present invention comprise an effective amount of a controlled release composition as discussed above dispersed in a pharmaceutically acceptable carrier or aqueous medium. Such compositions also are referred to as inocula. The phrases "pharmaceutically" or "pharmacologically acceptable" refer to compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

Solutions of therapeutic compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyl oleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components in the pharmaceutical composition are adjusted according to well known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

The therapeutic compositions of the present invention may include classic pharmaceutical preparations. Administration of therapeutic compositions according to the present invention will be via any common route so long as the target tissue is available via that route. This includes oral, nasal, buccal, rectal, vaginal or topical. Topical administration would be particularly advantageous for the treatment of skin cancers, to prevent chemotherapy-induced alopecia or other dermal hyperproliferative disorder. Alternatively, administration may be by orthotopic, intradermal subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, the preferred route is aerosol delivery to the lung. Volume of the aerosol is between about 0.01 ml and 0.5 ml. Similarly, a preferred method for treatment of colon-associated disease would be via enema. Volume of the enema is between about 1 ml and 100 ml.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the protection desired.

Precise amounts of the therapeutic composition also depend on the judgment of the practitioner and are peculiar to each individual. Factors affecting the dose include the physical and clinical state of the patient, the route of administration, the intended goal of treatment (alleviation of symptoms versus cure) and the potency, stability and toxicity of the particular therapeutic substance. Example 42 discusses anion binding compounds as therapeutic agents.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

The following examples are merely illustrative and not exhaustive. Examples of compositions useful in the present invention, along with their preparation are given. It is expected that one skilled in the art may appreciate that minor deviations may be incorporated without deviating from the scope of the present invention.

EXAMPLE 1

Synthesis of 1,2-Dipyrryl ethanedione

Oxalyl chloride (6.4 g, 0.05 mol) and dichloromethane (25 mL) were placed together under an argon atmosphere and stirred. Upon cooling to −78° C. in an acetone/$CO_2$ bath, dry pyridine (10 g, 0.12 mol) was added, resulting in the formation of a yellow precipitate. To this cooled suspension was added a solution of freshly distilled pyrrole (6.7 g, 0.1 mol) in dichloromethane (25 mL) by use of a canula. Immediately, the reaction mixture turns from yellow to brown. The reaction was allowed to stir for an additional 15 minutes at −60° C., after which time hydrochloric acid (5 M, 100 mL) was added to quench the reaction. The biphasic system is then separated and the organic phase was collected. The aqueous phase was extracted with dichloromethane (3×30 mL), and the combined organic phases were washed with water (100 mL), dried over anhydrous sodium sulfate, filtered and evaporated to dryness. This afforded a green precipitate. The crude product was further purified by silica gel column chromatography (acetone/hexanes (80/20 v/v)) to afford 10 (1.81 g, 38%) as a yellow powder.

Chracterization Data for 10

$^1$H NMR (250 MHz, DMSO $d_6$) δ6.26 (2H, dd, $J_1$=3.7 Hz, $J_2$=2.4 Hz, $H_\beta$), 6.89 (2H, dd, $J_1$=3.7 Hz, $J_2$=0.5 Hz, $H_{\beta pyrr}$), 7.30 (broad s, $H_{\alpha pyrr}$), 12.27 (2H, s, NH); $^{13}$C NMR (125 MHz, DMSO $d_6$) δ111.0, 120.9, 128.4, 128.6, 181.4.

EXAMPLE 2

Synthesis of 2,3-dypyrrylquinoxaline (1)

The synthesis of 2,3-dipyrrylquinoxaline (1) was carried out as follows. The diketone 10 (570 mg, 3.03 mmol) was dissolved in glacial acetic acid (70 mL) and to this was added a solution of ortho-phenylenediamine (715 mg, 6.62 mmol) in acetic acid (30 mL) with stirring. The resultant mixture was then brought to reflux for 90 min under an atmosphere of argon. After this time majority of the acetic acid was removed under vacuum and the residue was taken up in a mixture of water (30 mL) and dichloromethane (30 mL). The organic phase was separated off and the aqueous phase was extracted with further dichloromethane (2×20 mL). The organic phases were combined and washed with saturated aqueous sodium bicarbonate solution (50 mL), water and (50 mL) and brine (50 mL). After drying over anhydrous sodium sulfate, filtered and evaporated to dryness. The residue obtained was the purified using silica gel column chromatography (dichloromethane) to afford 1 (730 mg, 94%) as a yellow powder.

Oxalyl chloride, o-phenylenediamine, 4-nitro-1,2-diaminobenzene were purchased from Aldrich and used without further purification. 4,5-Diamino-1,2-dimethoxybenzene was prepared according to the method of Sessler, 1992. 4-5,-Dinitro-1,2-diaminobenzene was prepared according to the method of Cheeseman, 1962.

Characterization Data for 1

$^1$H NMR (250 MHz, $CDCl_3$) δ6.16 (2H, m, $H_{\beta 2}$), 6.82 (2H, m, $H_{\beta 1}$), 6.89 (2H, m, $H_\alpha$) 7.46 (2H, dd, $J_o$=12.5 Hz, $J_m$=2.9 Hz, $CH_{benz}$), 7.78 (2H, dd, $J_o$=12.5 Hz, $J_m$=2.9 Hz, $CH_{benz}$), 9.54 (2H, broad s, NH); $^{13}$C NMR (125 MHz, $CDCl_3$) δ109.9, 112.8, 121.1, 128.0, 128.8, 129.0, 139.6, 143.6; HRMS (CI+) m/z calcd for $C_{16}H_{13}N_4$: 261.11402, found: 261.11343; Anal. Calcd for $C_{16}H_{13}N_4 \cdot 0.5H_2O$: C, 71.35; H, 4.87; N, 20.80. Found C, 71.23; H, 4.79; N, 20.48.

EXAMPLE 3

Synthesis of 2,3-dipyrrol-2'-yl-6,7-dimethoxyquinoxaline (2)

4,5-Diamino-1,2-dimethoxybenzene (1.25 g, 7.45 mmol) and 1,2-dipyrrol-2'-ylethanedione (2 g, 10.65 mmol) were dissolved in acetic acid (250 mL) and heated at reflux under an atmosphere of argon overnight. The solvent was removed under vacuum and the residue was taken up in a mixture of water (50 mL) and dichloromethane (100 mL). The organic phase was separated off and the aqueous phase was extracted with further dichloromethane (2×40 mL). The organic phases were combined and washed with saturated aqueous sodium bicarbonate solution (50 mL), water (50 mL), then brine (50 mL). After drying over anhydrous sodium sulfate, the solution was filtered and evaporated to dryness. Final purification was then effected using silica gel column chromatography (methanolchloroform, 2:98) to afford 2,3-dipyrrol-2'-yl-6,7-dimethoxyquinoxaline (2.05 g, 86%) as a yellow/green powder: m.p. 196–198° C.; $^1$H NMR (250 MHz, DMSO $d_6$) δ3.98 (6H, s), 6.05–6.09 (2H, m), 6.11–6.15 (2H, m), 6.92–6.96 (2H, m), 7.32 (2H, s), 11.35 (2H, br s, NH); $^{13}$C NMR (62.5 MHz, $CDCl_3$) δ56.7, 106.5, 110.4, 112.1, 120.8, 129.7, 137.3, 142.3, 152.7; HRMS (CI+) m/z (M+1) calcd. for $C_{18}H_{17}N_4O_2$: 321.1352, found: 321.1358; UV-vis ($CH_2Cl_2$) $\lambda_{max}$ [nm] (ε): 272 (23 890), 292sh (17 850), 412 (15 900).

Characterization Data for 2 m.p. 196–198° C.; $^1$H NMR (250 MHz, DMSO $d_6$) δ3.98 (6H, s), 6.05–6.09 (2H, m), 6.11–6.15 (2H, m), 6.92–6.96 (2H, m), 7.32 (2H, s), 11.35 (2H, br s, NH); $^{13}$C NMR (125 MHz, $CDCl_3$) δ56.7, 106.5, 110.4, 112.1, 120.8, 129.7, 137.3, 142.3, 152.7; HRMS (CI+) m/z (M+1) calcd. for $C_{18}H_{17}N_4O_2$: 321.1352, found: 321.1358.

EXAMPLE 4

Synthesis of 2,3-dipyrrol-2'-yl-6,7-dinitroquinoxaline (3)

1,2-Dipyrrol-2'-ylethanedione (200 mg, 1.06 mmol) and 1,2-diamino-4,5-dinitrobenzene (265 mg, 1.34 mmol) were dissolved in glacial acetic acid (40 mL) and the resultant solution was heated at reflux in the dark for 4 h under an atmosphere of argon. The solution was allowed to cool and evaporated to dryness in vaccuo. The residue was taken up in dichloromethane (50 mL) and washed with sodium hydrogen carbonate solution (sat., 2×50 mL), brine (50 mL), dried over anhydrous sodium sulfate, filtered and evaporated to dryness. The residue was chromatographed over silica (chloroform) and the front running band was collected to afford 2,3-dipyrrol-2'-yl-6,7-dinitroquinoxaline (297 mg, 80%) as a red powder: m.p. 215–217° C.; $^1$H NMR (250 MHz, DMSO $d_6$) δ6.20–6.28 (2H, m, pyrrole H), 6.68–6.77 (2H, m, pyrrole H), 7.15–7.22 (2H, m, pyrrole H), 8.50 (2H, s, quinoxline H), 11.94 (2H, br s, NH); $^{13}$C NMR (62.5 MHz, DMSO $d_6$) δ109.9, 114.9, 124.6, 125.7, 127.9, 140.0, 140.7, 147.7; HRMS (CI+) m/z (M+1) calcd. for $C_{16}H_{11}N_6O_4$ 351.0842, found 351.0852; UV-vis ($CH_2Cl_2$) $\lambda_{max}$ [nm] (ε): 340 (29 100), 460 (29 200).

EXAMPLE 5

Synthesis of 6-nitro-2-3-dipyrrylquinoxaline (7)

1,2-Dipyrrol-2'-ylethanedione (175 mg, 0.93 mmol) and 4-nitro-1,2-diaminobenzene (245 mg, 1.60 mmol) were dissolved in glacial acetic acid (30 mL) and the resultant solution was heated at reflux in the dark overnight under an atmosphere of argon. The solution was allowed to cool and evaporated to dryness in vaccuo. The residue was taken up in dichloromethane (50 mL) and washed with sodium hydrogen carbonate solution (sat., 2×50 mL), brine (50 mL), dried over anhydrous sodium sulfate, filtered and evaporated to dryness. The residue was chromatographed over silica (chloroform) and the front running band was collected to afford 2,3-dipyrrol-2'-yl-6-nitroquinoxaline (240 mg, 85%) as a red powder: m.p. 206–208° C.; $^1$H NMR (250 MHz, DMSO $d_6$) δ6.15–6.25 (2H, m, pyrrole H), 6.45–6.60 (2H, m, pyrrole H), 7.07–7.19 (2H, m, pyrrole H), 8.05 (1H, d, J 9.1 Hz, H8 quinoxaline), 8.48 (1H, dd, J 9.1, 2.5 Hz, H7 quinoxaline), 8.65 (1H, d, J 2.5 Hz, H5 quinoxaline), 11.75 (1H, br s, NH), 11.86 (1H, br s, NH); $^{13}$C NMR (62.5 MHz, DMSO $d_6$) δ109.2, 109.6, 112.9, 114.1, 122.3, 122.6, 123.6, 123.7, 128.1, 128.3, 129.2, 137.8, 142.4, 146.3, 146.5, 147.0; HRMS (CI+) m/z (M+1) Calcd for $C_{16}H_{12}N_5O_2$ 306.0991, found 306.0996; UV-vis ($CH_2Cl_2$) $\lambda_{max}$ [nm] (ε): 325 (22 000), 370 (13 650), 450 (18 730); Anal. Calc. for $C_{16}H_{11}N_5O_2$: C, 62.95; H, 3.61; N, 22.95. Found C, 62.87; H, 3.67; N, 22.96.

EXAMPLE 6

Synthesis of Mono-2-(trimethylsilyl)ethoxymethyl (SEM) protected derivative (12)

2,3-Dipyrrylquinoxaline (400 mg, 1.54 mmol) was dissolved in N,N-dimethylformamide (30 ml) under an atmosphere of argon. Sodium hydride (60% dispersion in mineral oil, 100 mg) was added and the resultant mixture was allowed to stir at room temperature for 1 h. 2-(trimethylsilyl)ethoxymethyl chloride (SEM-Cl) (205 mg, 1.23 mmol) was then added and the mixture was stirred at room temperature for a further 90 min. The solvent was removed under vacuum and the residue was taken up in dichloromethane (150 ml) and washed with water (2×100 ml), and brine (100 ml). The organic phase was dried over sodium sulfate, filtered and evaporated to dryness. Final purification was then effected using silica gel column chromatography (toluene initially, then toluene/ethylacetate, 95/5) to afford 7 (40 mg, 6.6%) as a brown gum: $^1$H NMR (500 MHz, $CD_2Cl_2$) δ–0.70 (9H, s), 0.56–0.60 (2H, m), 3.23–3.27 (2H, m), 5.15 (2H, s), 5.78–5.80 (1H, m), 6.12–6.14 (1H, m), 6.34–6.37 (1H, m), 6.48–6.51 (1H, m), 6.96–6.98 (1H, m), 7.02–7.04 (1H, m), 7.63–7.67 (1H, m), 7.71–7.75 (1H, m) 7.98–7.82 (1H, m), 9.90–10.00 (1H, br s); $^{13}$C NMR (125 MHz, $CD_2Cl_2$) δ–1.6, 17.8, 30.1, 66.1, 77.0, 109.0, 111.0, 112.3, 113.1, 122.0, 123.4, 128.4, 128.8, 129.4, 130.6, 140.4, 141.2, 145.3, 146.0.

EXAMPLE 7

Preparation of 2,3-di-5'-bromopyrrol-2'-ylquinoxaline 2,3-Dipyrrol-2'-ylquinoxaline (1.5 g, 5.77 mmol) was dissolved in carbon tetrachloride (150 ml) and recrystallised N-bromosuccinimde (2.25 mg, 12.64 mmol) and benzoyl peroxide (40 mg) were added and the resultant mixture was heated at reflux under an atmosphere of argon in the dark overnight. The solvent was then removed under vacuum and the residue was chromatographed over silica (ethyl acetate/dichloromethane 5:95) and the major band was collected to afford 2,3-di-5'-bromopyrrol-2'-ylquinoxaline (1.7 g, 70%) as a light brown solid: m.p. 204–206° C.; $^1$H NMR (250 MHz, DMSO $d_6$) δ6.16–6.24 (4H, m, β-pyrrolic H), 7.73–7.81 (2H, m, aryl H), 7.95–8.03 (2H, m, aryl H), 12.3 (2H, broad s, NH); $^{13}$C NMR (62.5 MHz, DMSO $d_6$) δ101.9, 111.1, 112.8, 128.1, 129.6, 130.4, 139.5, 143.9; HRMS (CI+) m/z calcd for $C_{16}H_{11}N_4Br_2$: 416.93504, found: 416.93557; Anal. Calcd for $C_{16}H_{10}N_4Br_2$: C, 45.93; H, 2.39; N, 13.40. Found C, 46.09; H, 2.56; N, 13.49.

EXAMPLE 8

Preparation of 2,3-di-5'-iodopyrrol-2'-ylquinoxaline 2,3-Dipyrrol-2'-ylquinoxaline (500 mg, 1.92 mmol) and sodium acetate (1.04 g, 7.68 mmol) were dissloved in acetic acid (100 mL) and cooled to 0° C. in an ice bath. As the acetic acid began to crystallise, a solution of iodine monochloride (592 mg, 3.65 mmol) in acetic acid (10 mL) was added to the quinoxaline solution and the mixture was stirred for 10 min. A saturated solution of sodium thiosulfate (30 mL) was then added and the mixture was stirred at room temperature for 1 h. The mixture was then washed with ethyl acetate (100 mL) and the organic phase was separated off. The organic phase was washed with water (2×100 mL) and brine (100 mL), dried over anhydrous sodium sulfate, filtered and evaporated to dryness. The residue ws achromatographed over silica (dichloromethane/hexane 1:1, v/v) to afford 2,3-di-5'-iodopyrrol-2'-ylquinoxaline (830 mg, 84%).

EXAMPLE 9

Preparation of 2,3-di(5'-formylpyrrol-2'-yl) quinoxaline

Phosphorus oxychloride (240 μL, 2.57 mmol) was added to DMF (454 μL, 5.86 mmol) at 0° C. under an atmosphere of argon. This mixture was then allowed to warm to room temperature and stirred for 10 min before 1,2-dichloroethane (3 mL) was added. To this mixture was then added a solution of 2,3-dipyrrol-2'-ylquinoxaline (260 mg, 1.00 mmol) in 1,2-dichloroethane (3 mL) over a period of 10 min. The resulting mixture was heated at reflux for 30 min before being cooled to 0° C. A saturated aqueous solution of sodium acetate (3 mL) was then added and the mixture was heated at reflux for a further 30 min. Upon cooling, the mixture was washed with chloroform (2×50 mL) and the combined organic phases were then washed with water (2×50 mL), brine (50 mL), dried over anhydrous sodium sulfate, filtered and evaporated to dryness. The residue was then chromatographed over silica (dichloromethane initially, then dichloromethane/methanol, 99.5:0.5 v/v) to afford 2,3-di(5'-formylpyrrol-2'-yl)quinoxaline (216 mg, 68%) as a yellow solid.

EXAMPLE 10

Preparation of 2,3-di(5'-benzoylpyrrol-2'-yl) quinoxaline

Under an atmosphere of argon, N,N-dimethylbenzamide (1.20 g, 8.0 mmol) was added to 1,2-dichloroethane (5 mL) followed by the addition of phosphorus oxychloride (368 µL, 3.96 mmol) and and the mixture was stirred at room temperature for 30 min. To this mixture was added a solution of 2,3-dipyrrol-2'-ylquinoxaline (400 mg, 1.54 mmol) in 1,2-dichloroethane (50 mL) over a period of 20 min. The resulting mixture was heated at reflux for 24 h before being allowed to cool. An aqueous solution of sodium acetate (20 mL) was then added and the mixture was heated at reflux for a further 30 min. Upon cooling, the mixture was washed with dichloromethane (2×100 mL) and the combined organic phases were then washed with water (2×150 mL), brine (150 mL), dried over anhydrous sodium sulfate, filtered and evaporated to dryness. The residue was then chromatographed over silica (dichloromethane) to afford 2,3-di(5'-benzoylpyrrol-2'-yl)quinoxaline (314 mg, 44%).

EXAMPLE 11

Preparation of 2,3-dipyrrol-2'-yl-6,7-dipentoxyquinoxaline 4,5-Dipentoxy-1,2-diaminobenzene (1.12 g, 4.0 mmol) and 1,2-dipyrrol-2'-ylethanedione (500 mg, 2.66 mmol) were dissolved in acetic acid (80 ml) and the resulting mixture was first evacuated, and then placed under an atmosphere of argon and heated at reflux in the dark overnight. The mixture was allowed to cool and the solvent was removed under vacuum. The residue was then dissolved in dichlormethane (100 ml) and washed with sodium carbonate solution (100 ml), brine (100 ml), dried over anhydrous sodium sulfate and evaporated to dryness. The residue was then chromatographed over silica (dichloromethane) and the front running band was collected to afford 2,3-dipyrrol-2'-yl-6,7-dipentoxyquinoxaline (768 mg, 67%) as a yellow-green powder: m.p. 142–144° C.; $^1$H NMR (250 MHz, DMSO d$_6$) δ0.94 (6H, t, J 7.0 Hz, CH$_3$), 1.33–1.56 (8H, m, γ and δ CH$_2$), 1.84 (4H, app quin., β CH$_2$), 4.17 (4H, t, J 6.3 Hz, α CH$_2$), 6.03–6.08 (2H, m, pyrrole H), 6.09–6.14 (2H, m, pyrrole H), 6.90–6.95 (2H, m, pyrrole H), 7.25 (2H, s, quinoxaline H), 11.38 (2H, br s, NH); $^{13}$C NMR (62.5 MHz, DMSO d$_6$) δ13.9, 21.9, 27.8, 28.1, 68.4, 106.8, 108.6, 110.1, 120.2, 128.9, 151.4; HRMS (CI+) m/z (M+1) calcd. for C$_{26}$H$_{33}$N$_4$O$_2$ 433.2603, found 433.2613.

EXAMPLE 12

Preparation of 2,3-di(5'-bromopyrrol-2'-yl)-6-nitroquinoxaline 2,3-Dipyrrol-2'-yl-6-nitroquinoxaline (500 mg, 1.64 mmol) was dissolved in carbon tetrachloride (150 mL) and recrystallised NBS (613 mg, 3.44 mmol, 2.1 equiv.) and benzoyl peroxide (10 mg) were added. The resultant mixture was heated at reflux under an atmosphere of argon in the dark overnight. The mixture was allowed to cool and then evaporated to dryess. The residue was chrommatographed over silica (dichloromethane) to afford 2,3-di(5'-bromopyrrol-2'-yl)-6-nitroquinoxaline (226 mg, 30%) as a red solid.

EXAMPLE 13

Preparation of 2,3-dipyrrol-2'-yl-6-aminoquinoxaline 2,3-Dipyrrol-2'-yl-6-nitroquinoxaline (107 mg, 0.35 mmol) was dissolved in ethanol (20 mL) and palladium on carbon (10%, 10 mg) was added. The mixture was placed under an atmosphere of hydrogen and stirred overnight in the dark. The mixture was then filtered through celite and the filtrate was evaporated to dryness to afford 2,3-dipyrrol-2'-yl-6-aminoquinoxaline (90 mg, 93%) as an orange solid.

EXAMPLE 14

Preparation of 2,3-dipyrrol-2'-yl-6,7-diaminoquinoxaline 2,3-Dipyrrol-2'-yl-6,7-dinitroquinoxaline (90 mg, 0.25 mmol) was dissolved in absolute ethanol (40 mL) and 10% palladium on carbon (15 mg) was added. The resulting mixture was stirred under an atmosphere of hydrogen overnight in the dark. The solution was then filtered through celite and evaporated to dryness to afford crude 2,3-dipyrrol-2'-yl-6,7-diaminoquinoxaline (72 mg, 100%) and used without further purification.

EXAMPLE 15

Preparation of 2,3-dipyrrol-2'-yl-5-nitroquinoxaline 1,2-Dipyrrol-2'-ylethanedione (500 mg, 2.66 mmol) and 3-nitro-1,2-phenylenediamine (680 mg, 4.45 mmol) were dissolved in acetic acid (100 mL) and heated at reflux in the dark under an atmosphere of argon overnight. The solvent was removed under vacuum and the residue was dissolved in dichloromethane (150 mL), washed with sodium carbonate solution (2×100 mL) and brine (100 mL), dried over anhydrous sodium sulfate, filtered and evaporated to dryness. The crude material was then chromatographed over silica (dichloromethane) and the major front running band was collected to afford 2,3-dipyrrol-2'-yl-5-nitroquinoxaline (480 mg, 59%) as an orange solid: m.p. 183–185° C.; $^1$H NMR (250 MHz, DMSO d$_6$) δ6.15–6.22 (2H, m, pyrrole H), 6.39–6.47 (2H, m, pyrrole H), 7.05–7.10 (2H, m, pyrrole H), 7.76–7.84 (1H, m, quinoxaline H), 8.14–8.22 (2H, m, quinoxaline H), 11.41 (1H, br s, NH), 11.77 (1H, br s, NH); $^{13}$C NMR (62.5 MHz, DMSO d$_6$) δ109.3, 113.0, 113.4, 122.7, 123.0, 123.2, 127.6, 128.0, 128.1, 131.0, 131.9, 139.3, 145.9, 146.2; HRMS (CI+) m/z (M+1) Calcd for $C_{16}H_{12}N_5O_2$ 306.0991, found 306.0995.

EXAMPLE 16

Preparation of 2,3-dipyrrol-2'-yl-6-bromoquinoxaline 1,2-Dipyrrol-2'-ylethanedione (440 mg, 2.34 mmol) and 4-bromo-1,2-phenylenediamine (560 mg, 3.00 mmol) were dissolved in acetic acid (70 mL) and heated at reflux in the dark under an atmosphere of argon overnight. The solvent was removed under vacuum and the residue was dissolved in dichloromethane (150 mL), washed with sodium carbonate solution (2×100 mL) and brine (100 mL), dried over anhydrous sodium sulfate, filtered and evaporated to dryness. The crude material was then chromatographed over silica (dichloromethane) and the major front running band was collected to afford 2,3-dipyrrol-2'-yl-6-bromoquinoxaline (510 mg, 65%) as a brown/green solid: m.p. 144–146° C.; $^1$H NMR (500 MHz, DMSO $d_6$) δ6.12–6.15 (2H, m, pyrrole H), 6.28–6.30 (2H, m, pyrrole H), 6.98–7.02 (2H, m, pyrrole H), 7.80 (1H, dd, J 2.1, J 8.8 Hz, quinoxaline H), 7.85 (1H, d, J 8.8 Hz, quinoxaline H), 8.07 (1H, d, J 2.1 Hz, quinoxaline H), 11.57 (2H, br s, NH); $^{13}$C NMR (125 MHz, DMSO $d_6$) δ108.9, 109.1, 112.0, 112.2, 121.5, 121.8, 122.0, 128.3, 128.4, 129.1, 130.0, 132.0, 138.2, 140.1, 145.3, 145.7; MS (CI+) m/z (M+1) Calcd for $C_{16}H_{12}N_4Br$ 339.02453, found 339.02430.

EXAMPLE 17

Preparation of 2,3-diaminonaphthalene adduct 1,2-Dipyrrol-2'-yl ethanedione (200 mg, 1.06 mmol) and 2,3-diaminonaphthalene (252 mg, 1.59 mmol) were dissolved in glacial acetic acid (30 mL) and the resultant solution was heated at reflux under an atmosphere of argon in the dark overnight. The solution was allowed to cool and evaporated to dryness in vaccuo. The residue was taken up in dichloromethane (50 mL) and washed with sodium hydrogen carbonate solution (sat., 2×50 mL), brine (50 mL), dried over anhydrous sodium sulfate, filtered and evaporated to dryness. The residue was chromatographed over silica (dichloromethane) and the front running band was collected to afford the 2,3-diaminonaphthalene adduct (156 mg, 95%) as a light brown solid: m.p. 184–186° C.; $^1$H NMR (250 MHz, DMSO $d_6$) δ6.15–6.20 (2H, m, pyrrole H), 6.34–6.39 (2H, m, pyrrole H), 7.03–7.08 (2H, m. pyrrole H), 7.55–7.64 (2H, m), 8.15–8.23 (2H, m), 8.54 (2H, s), 11.71 (2H, br s, NH); $^{13}$C NMR (62.5 MHz, DMSO $d_6$) δ108.9, 112.6, 122.0, 125.6, 126.3, 128.2, 129.0, 133.0, 136.7, 145.8; HRMS (CI+) m/z (M+1) Calcd for $C_{20}H_{15}N_4$ 311.12967, found 311.12963.

EXAMPLE 18

Preparation of 9,10-diaminophenanthrene adduct 1,2-Dipyrrol-2'-yl ethanedione (500 mg, 2.66 mmol) and 9,10-diaminophenanthrene (830 mg, 3.99 mmol) were dissolved in glacial acetic acid (150 mL) and the resultant mixture was heated at reflux under an atmosphere of argon in the dark overnight. The mixture was allowed to cool and evaporated to dryness in vaccuo. The residue was chromatographed over silica (diclhoromethane) and the front running band was collected to afford the 9,10-diaminophenanthrene adduct (687 mg, 72%) as a light brown solid. HRMS (CI+) m/z (M+1) Calcd for $C_{24}H_{17}N_4$ 361.14532, found 361.14525.

EXAMPLE 19

Preparation of 2,3-dipyrrol-2'-yl-6-carboxyquinoxaline 1,2-Dipyrrol-2'-ylethanedione (500 mg, 2.66 mmol) and 3,4-diaminobenzoic acid (404 mg, 2.66 mmol) were dissolved in glacial acetic acid (80 mL) and the resultant solution was heated at reflux in the dark overnight. The solution was allowed to cool and evaporated to dryness in vaccuo. The residue was taken up in ethyl acetate (150 mL) and washed with hydrochloric acid (3 M, 80 mL), brine (80 mL), dried over anhydrous sodium sulfate, filtered and evaporated to dryness. The residue was chromatographed over silica (ethyl acetate/dichloromethane, 3:2 v/v) and the major band was collected to afford 2,3-dipyrrol-2'-yl-6-carboxyquinoxaline (270 mg, 33%). $^1$H NMR (250 MHz, DMSO $d_6$) δ6.14–6.21 (2H, m, pyrrole H), 6.35–6.43 (2H, m, pyrrole H), 7.02–7.09 (2H, m, pyrrole H), 8.00 (1H, d, J 8.7 Hz, H8 quinoxaline), 8.17 (1H, dd, J 8.7, 1.9 Hz, H7 quinoxaline), 8.49 (1H, d, J 2.5 Hz, H5 quinoxaline), 11.66 (1H, br s, NH), 11.73 (1H, br s, NH), 13.40 (1H, br s, $CO_2H$); $^{13}$C NMR (62.5 MHz, DMSO $d_6$) δ109.0, 109.3, 112.1, 112.8, 121.8, 122.5, 128.1, 128.4, 128.5, 129.9, 130.6, 138.5, 141.5, 145.8, 146.3, 166.8, HRMS (CI+) m/z (M+1) Calcd for $C_{17}H_{13}N_4O_2$ 305.1039, found 305.1035.

EXAMPLE 20

Preparation of 2,3-dipyrrol-2'-yl-6-carboxyquinoxaline octylester 2,3-Dipyrrol-2'-yl-6-carboxyquinoxaline (100 mg, 0.33 mmol) and octanol (47 mg, 0.36 mmol) were dissolved in dichloromethane (20 mL). To this solution was added DCC (82 mg, 0.40 mmol) and DMAP (2.5 mg, 0.02 mg) in dichloromethane (10 mL) over a 10 min period and the resulting mixture was stirred at room temperature for 4 h. The mixture was then evaporated to dryness and chromographed over silica (dichloromethane) to afford 2,3-dipyrrol-2'-yl-6-carboxyquinoxaline octyl ester (76 mg, 55%) as a yellow/green solid.

EXAMPLE 21

Preparation of 2,3-dipyrrol-2'-yl-6-carbxyamidoaquinoxaline-4"-benzo-18-crown-6

2,3-Dipyrrol-2'-yl-6-carboxyquinoxaline (100 mg, 0.33 mmol) was dissolved in a mixture of dichloromethane (10 mL) and N,N-diisopropylethylamine (100 mg, 0.724 mmol) and HBTU (137 mg, 0.362 mmol) was added. The resulting mixture was stirred for 5 min prior to the addition of a solution of 4-aminobenzo-18-crown-6 (118 mg, 0.36 mmol) in dichloromethane (6 mL). The reaction mixture was allowed to stir under an atmosphere of argon in the dark overnight. The mixture was then evaporated to dryness and the residue was chromatographed over silica (ethyl acetate initially, then methanol/ethyl acetate, 5:95 v/v) to afford 2,3-dipyrrol-2'-yl-6-carbxyamidoaquinoxaline-4"-benzo-18-crown-6 (150 mg, 74%).

EXAMPLE 22

Preparation of 2,3-dipyrrol-2'-yl-6-carboxyquinoxaline coupled to a bead 2,3-Dipyrrol-2'-yl-6-carboxyquinoxaline (45 mg, 0.14 mmol), HBTU (62 mg, 0.16 mmol), N,N- diisopropylethylamine (50 mg, 0.36 mmol) and DMF (0.5 mL) were added to dichloromethane (7 mL). This solution was then added to pre-swelled TG-amino resin (the resin was successively rinsed with DMF, then dichloromethane and then methanol several times). The mixture was stirred overnight and then filtered under vacuum and washed successively with dichoromethane, DMF, dichoromethane, DMF, dichoromethane, methanol, dichoromethane, and finally two rinses with methanol. After the third wash the solutions were colourless. The beads were then dried under vacuum for 4 days without further purification.

EXAMPLE 23

1,2-Di(3',4'-difluoropyrrol-2'-yl)ethanedione

Oxalyl chloride (800 µL, 8.64 mmol) and dichloromethane (15 mL) were placed together under an argon atmosphere and stirred. Upon cooling to −78° C. in an acetone/$CO_2$ bath, dry pyridine (1.28 mL, 15.8 mmol) was added, resulting in the formation of a yellow precipitate. To this cooled suspension was added a solution of 3,4-difluoropyrrole (1.49 g, 14.4 mmol) in dichloromethane (3 mL) via syringe. The reaction was allowed to stir for 3 h at −60° C., and then warmed to 0° C. over a 4 h period. The solution was then diluted with dichloromethane (20 mL) and washed with hydrochloric acid (3 M, 2×50 mL). The biphasic system was separated off and the organic phase was collected and washed with water (50 mL) and brine (50 mL). The organic phase was then dried over anhydrous sodium sulfate, filtered and evaporated to dryness. The acidic aqueous phase from the initial extraction was extracted with ethyl acetate (50 mL). The organic phase was separated off and washed with brine (100 ml), dried over anhydrous sodium sulfate, filtered and evaporated to dryness. This afforded a green precipitate which was purified by silica gel column chromatography (dichloromethane/ethyl acetate, 95:5 to 90:10 (v/v) as eluent) to afford 1,2-di(3',4'-difluoropyrrol-2'-yl)ethanedione (405 mg, 21%) as a yellow powder: m.p. 260–263° C. decomposed; $^1$H NMR (500 MHz, DMSO $d_6$) δ7.43–7.46 (2H, m), 12.36 (2H, br s, NH); $^{13}$C NMR (125 MHz, DMSO $d_6$, $^{19}$F decoupled) δ110.7 (m), 113.3 (d, J 192 Hz),136.8 (dd, J 9.1, 1.5 Hz), 141.0 (t, J 8.2 Hz), 178.8; $^{19}$F NMR (470 MHz, DMSO $d_6$) δ−164.1, −177.9; HRMS (CI+) m/z (M+1) calcd for $C_{10}H_5N_2O_2F_4$: 261.0287, found: 261.0288.

EXAMPLE 24

2,3-Di(3',4'-difluoropyrrol-2'-yl)quinoxaline 1,2-Di(3',4'-difluoropyrrol-2'-yl)ethanedione (112 mg, 0.43 mmol) and ortho-phenylenediamine (125 mg, 1.15 mmol) were dissolved in glacial acetic acid (20 mL). The resultant mixture was then heated at reflux under an atmosphere of argon in the dark overnight. The reaction mixture was evaporated to dryness under vacuum and the residue obtained was purified using silica gel column chromatography (dichloromethane eluent) to afford 2,3-di(340 ,4'-difluoropyrrol-2'-yl)quinoxaline (133 mg, 93%) as a yellow-green powder: m.p. 188–192° C.; $^1$H NMR (500 MHz, DMSO $d_6$) δ6.94–6.98 (2H, m, pyrrole H), 7.80–7.94 (2H, m, quinoxaline H), 8.01–8.05 (2H, m, quinoxaline H), 11.47 (2H, broad s, NH); $^{13}$C NMR (125 MHz, DMSO $d_6$, $^{19}$F decoupled) δ104.0 (d, J 22 Hz), 111.1 (d, J 16 Hz), 128.3, 130.3, 136.3 (dd, J 244, 11 Hz), 137.6 (dd, J 235, 11 Hz), 139.7, 142.4; $^{19}$F NMR (470 MHz, DMSO $d_6$) δ−172.6 (dt, J 12.2, 3.3 Hz), −180.5 (dt, J 12.6, 3.3 Hz); HRMS (CI+) m/z (M+1) calcd for $C_{16}H_9N_4F_4$: 333.0763, found: 333.0754; Anal. Calcd for $C_{16}H_8N_4F_4$: C, 57.84; H, 2.43; N, 16.86. Found C, 57.71; H, 2.50; N, 16.81.

EXAMPLE 25

2,3-Di(3',4'-difluoropyrrol-2'-yl)-6-nitroquinoxaline 1,2-Di(3',4'-difluoropyrrol-2'-yl)ethanedione (98 mg, 0.38 mmol) and 4-nitro-1,2-diaminobenzene (115 mg, 0.75 mmol) were dissolved in glacial acetic acid (30 mL) and the resultant solution was heated at reflux in the dark overnight under an atmosphere of argon. The solution was allowed to cool and evaporated to dryness in vaccuo. The residue was chromatographed over silica (chloroform) and the front running band was collected to afford 2,3-di(3',4'-difluoropyrrol-2'-yl)-6-nitroquinoxaline (120 mg, 84%) as a red powder: m.p. 217–219° C. with decomposition; HRMS (CI+) m/z (M+1) Calcd for $C_{16}H_7N_5F_4O_2$ 378.06141, found 378.06206.

EXAMPLE 26

Preparation of 1,2-di(5'-ethoxycarbonyl-3',4'-dimethylpyrrol-2'-yl)ethanedione

A solution of 5'-ethoxycarbonyl-3',4'-dimethylpyrrole (500 mg, 2.99 mmol) in dry dichloromethane (10 mL) was cooled in an ice bath under an atmosphere of argon. To this solution was added oxalyl chloride (220 mg, 1.79 mmol) and the solution was allowed to cool prior to the addition of tin(IV) chloride (857 mg, 380 µL, 3.29 mmol). The resultant mixture was stirred at 0° C. for 1 h and then allowed to warm to room temperature over 1 h. The solution was then washed with water (2×50 mL), brine (50 mL), dried over anhydrous sodium sulfate, filtered and evaporated to dryness. The crude residue was then recrystallised from a mixture of ethyl acetate/hexane, 1:9 v/v to afford 1,2-di(5'-ethoxycarbonyl-3',4'-dimethylpyrrol-2'-yl)ethanedione as a light green powder (128 mg, 22%): m.p. 210–212° C.; $^1$H NMR (500 MHz, $CDCl_3$) δ1.39 (6H, t, J 7.1 Hz), 2.27 (6H, s), 2.34 (6H, s), 4.38 (4H, q, J 7.1 Hz), 10.93 (2H, br s, NH); $^{13}$C NMR (125 MHz, $CDCl_3$) δ9.7, 11.2, 14.4, 61.0, 125.1, 126.9, 127.6, 133.4, 160.7, 179.5; HRMS (CI+) m/z (M+1) calcd for $C_{20}H_{25}N_2O_6$: 389.17126, found: 389.17092.

EXAMPLE 27

Preparation of 1,2-di(4'-acetyl-3',5'-dimethylpyrrol-2'-yl)ethanedione

A solution of 2,4-dimethyl-3-acetylpyrrole (1.48 g, 10.8 mmol) in dry ether (180 mL) was cooled in an ice bath under an atmosphere of argon. To this solution was added oxalyl chloride (720 µL, 8.1 mmol) and the solution was then stirred at 0° C. for 1 h, then allowed to warm to room temperature. The resultant dark-red–purple precipitate was then collected on a frit and the filtrate was removed and the precipitate was then washed with dichloromethane (30 mL). Mass spectral analysis revealed that the initial filtrate contained very little of the desired compound, however peaks at m/z (M+1) 210 and 228 can be attributed to monocondensation with oxalyl chloride, followed by hydrolysis of the acid chloride to the acid, and mono-condensation product with oxalyl chloride respectively. The dichloromethane washings of the precipitate contained essentially only the desired product. The precipitate itself also contained essentially only the desired 1,2-di(4'-acetyl-3',5'-dimethylpyrrol-2'-yl)ethanedione (420 mg, 24%) as a purple solid. $^1$H NMR (250 MHz, DMSO d$_6$) δ2.28 (3H, s), 2.40 (3H, s), 2.53 (3H, s), 11.74 (2H, br s, NH); $^{13}$C NMR (125 MHz, DMSO d$_6$) δ12.3, 14.5, 31.3, 123.5, 124.9, 132.0, 143.1, 183.4, 194.6, HRMS (CI+) m/z (M+1) calcd for C$_{18}$H$_{21}$N$_2$O$_4$: 329.15013, found: 329.15075.

EXAMPLE 28

2,3-Di(3',5'-dimethyl-4'acetylpyrrol-2'-yl)-6-nitroquinoxaline 1,2-Di(4'-acetyl-3',5'-dimethylpyrrol-2'-yl)ethanedione (100 mg, 0.30 mmol) and 4-nitro-1,2-diaminobenzene (79 mg, 0.52 mmol) were dissolved in glacial acetic acid (15 mL) and the resultant solution was heated at reflux in the dark overnight under an atmosphere of argon. The solution was allowed to cool and the evaporated to dryness in vaccuo. The residue was then taken up in chloroform (70 mL) and washed with hydrochloric acid (3 M, 3×40 mL), water (50 mL), sodium bicarbonate solution (60 mL), brine (70 mL). The organic phase was then dried over anhydrous sodium sulfate, filtered and evaporated to dryness to afford 34 mg of crude material.

EXAMPLE 29

Preparation of 1,2-di(4'-heptanoyl-3',5'-dimethylpyrrol-2'-yl)ethanedione

A solution of 2,4-dimethyl-3-heptanoylpyrrole (500 mg, 2.41 mmol) in dry dichloromethane (10 mL) was cooled in an ice bath under an atmosphere of argon. To this solution was added oxalyl chloride (183 mg, 1.44 mmol, 125 μL) and the solution was then stirred at 0° C. for 1 h, then at r.t. for 2 h. The reaction mixture was diluted with dichloromethane (50 mL), and then washed with water (2×30 mL), brine (30 mL), dried over anhydrous sodium sulfate, filtered, and evaporated to dryness. Mass spec analysis of the crude product indicated the presence of the desired compound, 1,2-di(4'-heptanoyl-3',5'-dimethylpyrrol-2'-yl)ethanedione. No further purification was attempted. (CI+) m/z (M+1) C$_{28}$H$_{41}$N$_2$O$_4$ requires 469; 208 (70), 252 (40), 280 (100), 298 (45), 469 (45). (CI−) m/z C$_{28}$H$_{40}$N$_2$O$_4$ requires 468; 278 (28), 468 (100).

EXAMPLE 30

Preparation of 2,3-dipyrrol-2'yl-5,6-dicyanopyrazine

Diaminomaleonitrile (348 mg, 3.22 mmol) and 1,2-dipyrrol-2'-yl ethanedione (500 g, 2.66 mmol) were dissolved in acetic acid (70 mL) and heated at reflux under an atmosphere of argon for overnight in the dark. The solvent was removed under vacuum and the residue was taken up in a mixture of water (50 mL) and dichloromethane (100 mL). The organic phase was separated off and the aqueous phase was extracted with further dichloromethane (2×40 mL). The organic phases were combined and washed with saturated aqueous sodium bicarbonate solution (50 mL), water (50 mL), then brine (50 mL). After drying over anhydrous sodium sulfate, the organic phase was filtered and evaporated to dryness. Final purification was then effected using silica gel column chromatography (dichloromethane) to afford 2,3-dipyrrol-2'yl-5,6-dicyanopyrazine (65 mg. 10%).

$^1$H NMR (250 MHz, DMSO d$_6$) 6.17δ–6.25 (2H, m), 6.82–6.88 *2H, m), 7.12–7.18 (2H, m), 11.96 (2H, br s, NH); $^{13}$C NMR (62.5 MHz, CDCl$_3$) δ110.2, 114.5, 114.7m, 125.4, 126.3, 144.0; HRMS (CI+) m/z (M+1) calcd. For C$_{14}$H$_9$N$_6$: 261.08887, found: 261.08869.

EXAMPLE 31

Structure Determination of Fluoride Complexes

X-ray Structure Analysis

Figure 2:
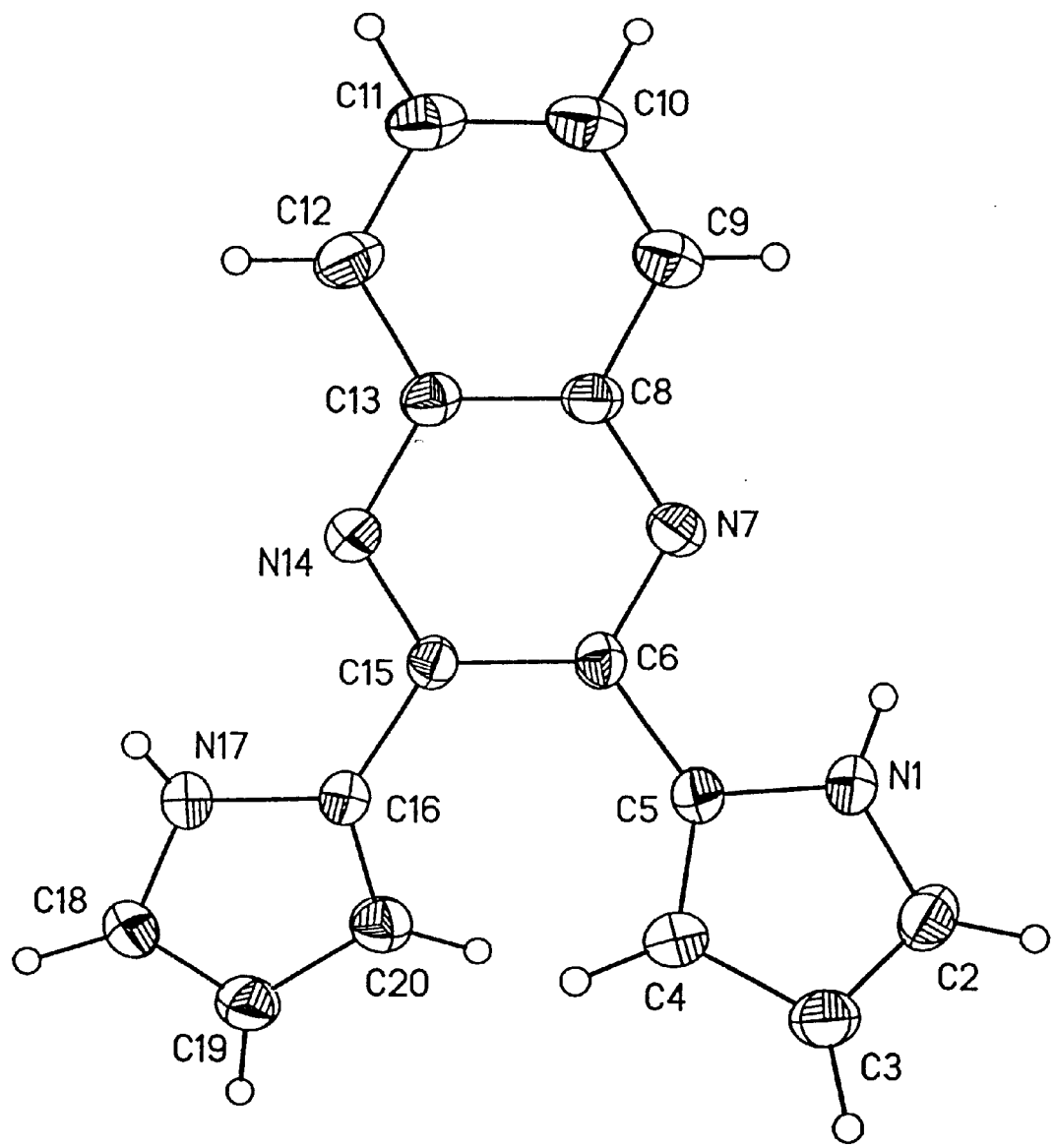
FIG. 2 is a view of the 2,3-dipyrrylquinoxaline unit 1 in its anion-free water complex.

The molecular structure of compound 1 as well as its corresponding tetrabutylammonium fluoride complex ([1.F]$^-$) were deduced from single crystal X-ray diffraction analyses. The requisite single crystals were obtained from the slow evaporation of dichloromethane/methanol (90/10: v/v) and neat dichloromethane solutions of 1 and [1.F]$^-$. (Bu)$_4$N$^+$ respectively. In both cases, the quinoxaline moiety was found to possess the expected planar structure. As shown in FIG. 1 and FIG. 2, the two pyrrole subunits were found to be rotated in such a way that they point out, in opposite directions, towards the exterior of the system.

While the structures of the fluoride complex and anion-free receptor are quite similar, a major difference involves the hydrogen bonding network. The fluoride complex [1.F]$^-$ presents a network that involves 1) two pyrrolic NH subunits derived from two distinct dipyrrylquinoxaline units, 2) a fluoride anion and 3) a molecule of water. The net result is a planar network, wherein two identical planes are separated by a layer of tetrabulammonium cations, as shown in FIG. 1. By contrast, the structure of the fluoride-free system reveals a hydrogen bonding network that serves to arrange the dipyrrylquinoxaline moieties into layers wherein a molecule of water bridges two pyrrolic NH groups from two distinct molecules. In this instance, it is also worth noting that, in addition to the conventional N . . . O hydrogen bonding interactions, one hydrogen atom of the bridging water molecule is directed at the centroid of a pyrrole ring. The result of this interaction is that the molecules from two different planes are related by a two-fold screw axis.

In the case of the fluoride complex [1.F]$^-$, the tightness of the hydrogen bonds is highlighted by the short F . . . N distance: These distances are 2.629(2) and 2.640(2) Å respectively, and are, in fact, shorter than the corresponding F . . . N distances (2.790(2) Å) observed in the case of calixpyrrole fluoride anion complex (Dietrich, et al., 1981).

EXAMPLE 32

Spectroscopic Studies-Colormetric Assay for Anion Binding

The conclusion that 1 binds fluoride anion in dichloromethane solution was further supported by mass spectrometric analyses and titration experiments made using UV-visible absorption and fluorescence emission methods (Tables 1 and 2). The latter studies, which provided K$_a$ values (Tables 1 and 2), were complemented by molar ratio analyses (Job plots) with 1:1 binding stoichiometries observed in all cases.

In order to analyze compounds having only one pyrrolic nitrogen, a mono SEM protected analogue (12) was prepared as described in Example 6. Additionally, quinoxaline (11) was used in the analysis.

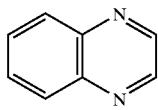

11

The results are as shown in the following tables:

stabilizing the complex via ancillary hydrogen bonding interactions involving the two HOP-phosphate protons.

Unfortunately, the fluorescence quantum yield of 10 is low. Thus we considered that 2,3-dipyrrylquinoxaline system 1 derived from it as well as its analogues 2, 3, and 7 might prove to be far better sensors. Not only should they display high affinities toward fluoride anion in dichloromethane solution, but they were expected to exhibit even more dramatic fluoride anion induced color changes as

TABLE 1

Spectroscopic properties of 2,3-dipyrrylquinoxaline 1, dipyrryl ethanedione 10, 6,7-dimethoxy-2,3-dipyrrylquinoxaline 2, 6,7-dinitro-2,3-dipyrrylquinoxaline 3, 6-nitro-2,3-dipyrrylquinoxaline 7, and quinoxaline 11. All values measured in dichloromethane.

| | 2,3-di-pyrryl quinoxaline 1 | Dipyrryl ethane-dione 10 | Di-methoxy 2 | Mono-nitro 7 | Dinitro 3 | MonoSEM-2,3-di-pyrrylquin-oxaline 12 | Quin-oxaline 11 |
|---|---|---|---|---|---|---|---|
| $\lambda_{max}(ex)$ | 412 nm | 341 nm | 414 nm | 450 nm | 460 nm | 396 nm | 315 nm |
| $\lambda_{max}(em)^a$ | 490 nm | 458 nm | 475 nm | 600 nm | 620 nm | 492 nm | 403 nm |
| $\epsilon$ (at $\lambda_{max}$) | 17,110 $M^{-1}cm^{-1}$ | 16,200 $M^{-1}cm^{-1}$ | 15,900 $M^{-1}cm^{-1}$ | 18,730 $M^{-1}cm^{-1}$ | 29,200 $M^{-1}cm^{-1}$ | 14860 $M^{-1}cm^{-1}$ | 6,222 $M^{-1}cm^{-1}$ |

[a]Fluorescence emission scan parameters: excitation at $\lambda_{max}$, 240 nm/min., emission slit width = 5 μm, excitation slit width = 5 μm.

TABLE 2

Anion binding constants ($K_a$) for 2,3-dipyrrylquinoxalines 2, 3 and 7 and control compounds 1, 10 and 11.[a]

| Anion | 2-3 dipyrrylquin-oxaline 1[b] | Dipyrryl ethanedione 10[c] | Dimethoxy 2 | Mononitro 7 | Dinitro 3 | Mono SEM-2,3-dipyrryl quinoxaline 12 |
|---|---|---|---|---|---|---|
| $F^-$ | 18,200 $M^{-1}$ | 23,000 $M^{-1}$ | 2,300 $M^{-1}$ | 118,000 $M^{-1}$ | 117,000 $M^{-1}$ | 2,300 $M^{-1}$ |
| $H_2PO_4^-$ | 60 $M^{-1}$ | 170 $M^{-1}$ | <50 $M^{-1}$ | 80 $M^{-1}$ | 55 $M^{-1}$ | <50 $M^{-1}$ |
| $Cl^-$ | 50 $M^{-1}$ | <50 $M^{-1}$ | <50 $M^{-1}$ | 45 $M^{-1}$ | 45 $M^{-1}$ | <50 $M^{-1}$ |

[1]All errors are ± 10%. All binding constants are reported as the average of 2–4 trials.
[b]Binding constants determined by fluorescence quenching: $\lambda_{ex}$ = 412 nm, $\lambda_{em}$ = 420–750 nm, 240 nm/min, emission slit width = 5 μm, excitation slit width = 5 μm.
[c]Binding constants were determined from UV-vis absorbance titration measurements monitoring the spectral changes occurring at 341 nm.

In terms of specifics, we found that in dichloromethane solution, the diketone precursor, 10, displays a relatively large extinction coefficient whereas its fluorescence emission is minimal. Under the same conditions, quinoxaline itself, 11, displays a relatively low extinction coefficient. Nonetheless, even with these control systems the addition of tetrabutylammonium salts of various anions ($F^-$, $Cl^-$ and $H_2PO_4^-$), gave rise to results that were quite interesting. In the case of 11 (in dichloromethane), the addition of $F^-$, $Cl^-$ and $H_2PO_4^-$ did not induce any significant change in the absorbance or emission spectra. By contrast, in the case of 10 remarkable changes were noticed in the emission spectra when either $F^-$ or $H_2PO_4^-$ were added. As a matter of fact, in the presence of $F^-$, a significant decrease and a shift in the absorbance intensity could be observed visually with the color of the solution changing from yellow-green to orange. Such effects can be rationalized in terms of the electron withdrawing nature of the two carbonyl groups, which serve to pull the electrons from the pyrrole units and thus act to increase the acidity of the pyrrolic NH protons. As a result, hydrogen bonding interactions with $F^-$ are favored. In the particular case of inorganic phosphate, we speculate that the two carbonyl groups may also be involved in binding, measured by absorption and emission spectroscopy, as well as naked eye color detection. As summarized in Table 2, this expectation is indeed realized in the case of 1, 3, and 7, with the latter two systems showing very dramatic yellow to purple fluoride anion-induced colorimetric responses.

The greater "success" of 3 and 7 relative to 1 and 2, a system that hardly "works" at all in terms of colorimetric $F^-$ signaling, is not really surprising considering that the relative electron deficiency of the mono- and dinitro derivatives should lead to increase in their hydrogen bonding donating character. Indeed, both 3 and 7 display affinity constants ($K_a$), for $F^-$ binding in dichloromethane (ca $10^5$ $M^{-1}$), that are quite high. By contrast, 1 ($K_a=2\times10^4$ $M^{-1}$) and 2 ($K_a=2\times10^3$ $M^{-1}$) display affinity constant that are much lower. Interestingly, even in the case of the high affinity systems 3 and 7 an excellent selectivity for fluoride anion is maintained; indeed, the selectivity ratio for $F^-$ over $Cl^-$ is more than 360.

In addition to the specific pyrrole-quinoxalines, the usefulness of the general pyrrole-aryl structures as sensing compounds has been demonstrated. Using 2,3-dipyrrol-2'yl-5,6dicyanopyrazine (preparation is described in Example 30) as a sensing compound, a vivid yellow-to-red color change in solution observed upon addition of fluoride ion verifies that the quinoxaline backbone is not essential for chemical sensing in this family of compounds. This is consistent with the theory that changes in orbital overlap between the pi systems of conjugated bridging unit and the pyrrole rings account for the sensitivity of the sensing elements to analyte species.

EXAMPLE 33

Mechanistic Studies of Fluoride Anion Binding

In order to understand more fully the above results, studies were performed to map out the mode of fluoride anion binding. Firstly, it was verified that two pyrrolic nitrogens are required to observe the anion-induced color change. Toward this end, the mono protected 2,3-dipyrrylquinoxaline 12 was prepared by reacting 0.8 equivalents of SEMCl with one equivalent of 2,3-dipyrrylquinoxaline. (See Scheme 2 illustrating mono SEM protection of 2,3-dipyrrylquinoxaline.) In dichloromethane, this mono-protected adduct showed no color change when treated with tetrabutyl ammonium fluoride.

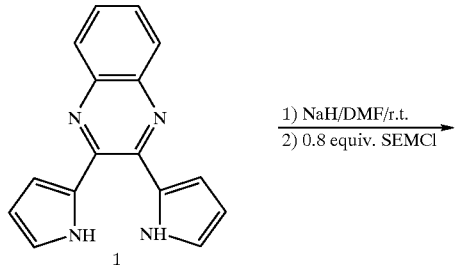

Scheme 2

The next series of mechanistic studies involved carrying out temperature dependent NMR measurements (room temperature to −80° C.). These revealed little out of the ordinary (i.e., no temperature dependent chemical shift changes were observed) and are consistent with a single atropisomer of 1 being present in solution. Further studies involve X-ray diffraction analysis with the realties as shown in Table 3.

TABLE 3

Selected bond distances (Å) and bond angles from X-ray

|  | 1 | [1 · F] |
|---|---|---|
| N-H ... H-N | 6.562 | 6.892 |
| N ... N | 5.766 | 5.763 |
| $H_\alpha$ ... $H_\alpha$ | 8.795 | 8.746 |
| $H_{\beta2}$ ... $H_{\beta2}$ | 2.607 | 2.612 |
| F ... H-N1 | — | 1.639 |
| F ... H-N2 | — | 8.196 |

EXAMPLE 34

Analogues of Pyrrole-Aryls for Metal Binding and Altered Fluorescence Properties Analogues of the pyrrole-aryls may be prepared to form metal complexes as shown below. By reaction of 9 with a 1,10-phenanthroline-5,6-dione, a compound represented by 13 may be synthesized. Compounds exemplified by 13 and 14 are contemplated for the ability to complex a metal through the phenanthroline unit.

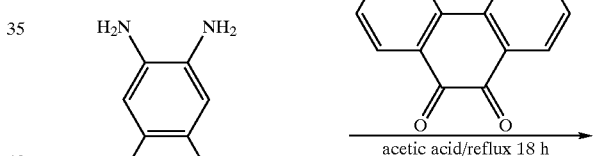

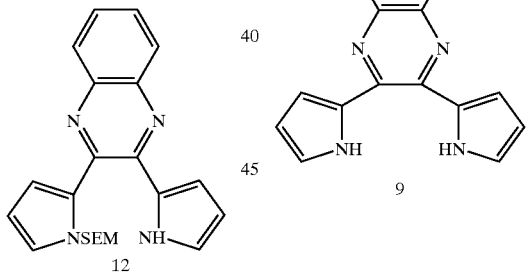

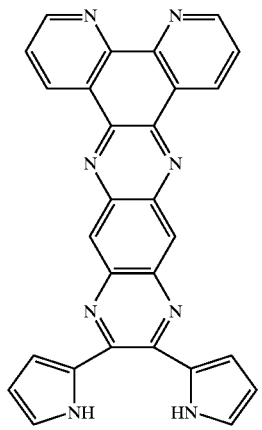

Scheme 3B

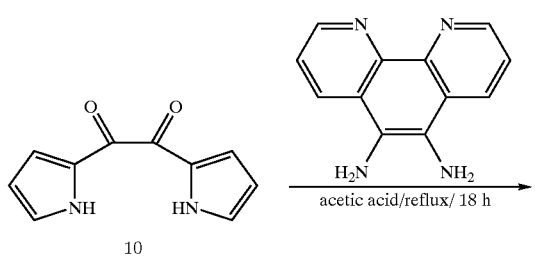

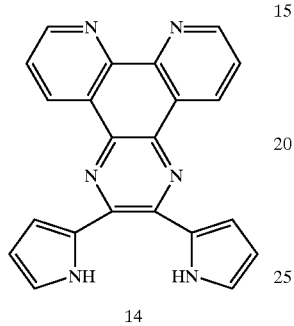

Similar analogues may be synthesized using the appropriate 1,2-diamines to produce compounds such as 15 and 16 for altered fluorescence /binding properties.

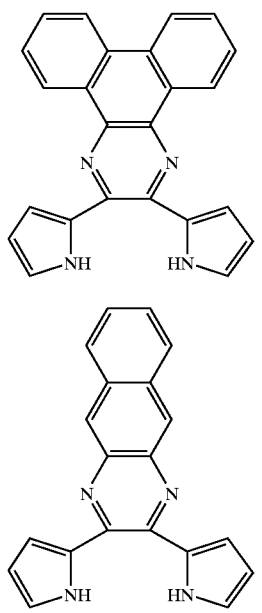

Additionally, using a porphyrin 1,2-diones, compounds exemplified by structure 17 can be generated as shown below:

17 wherein $R_1$–$R_{10}$ are as described previously and representative metals include Li, B, Na, Mg, Al, Si, K—As, Rb—Sb, Cs—La, Hf—Bi, pr, Eu, Yb and Th.

EXAMPLE 35

Post-Synthetic Modification of the 'Parent' 2,3-Dipyrrol-2'-yl-quinoxaline

A wide variety of substituents may be introduced to the pyrrole quinoxaline post-synthetically at the α-pyrrolic positions as shown with the following selected examples.

18

1: $R_1$=$R_2$=H
2: $R_1$=$R_2$=OMe
3: $R_1$=$R_2$=$NO_2$
4: $R_1$=$R_2$=$CH_3$
5: $R_1$=$R_2$=$O(CH_2CH_2O)_3CH_3$
6: $R_1$=$R_2$=$O(CH_2)_nCH_3$
7: $R_1$=H, $R_2$=$NO_2$
8: $R_1$=$NH_2$, $R_2$=$NO_2$
9: $R_1$=$NH_2$, $R_2$=$NH_2$
n=1–10 with any of $R_1$–$R_2$, $R_3$–$R_4$ may be as follows:
$R_3$=$R_4$=I, $R_3$=$R_4$=Br, $R_3$=$R_4$=$COCH_3$, $R_3$=$R_4$=CHO
As shown in Scheme 4 below.

Scheme 4

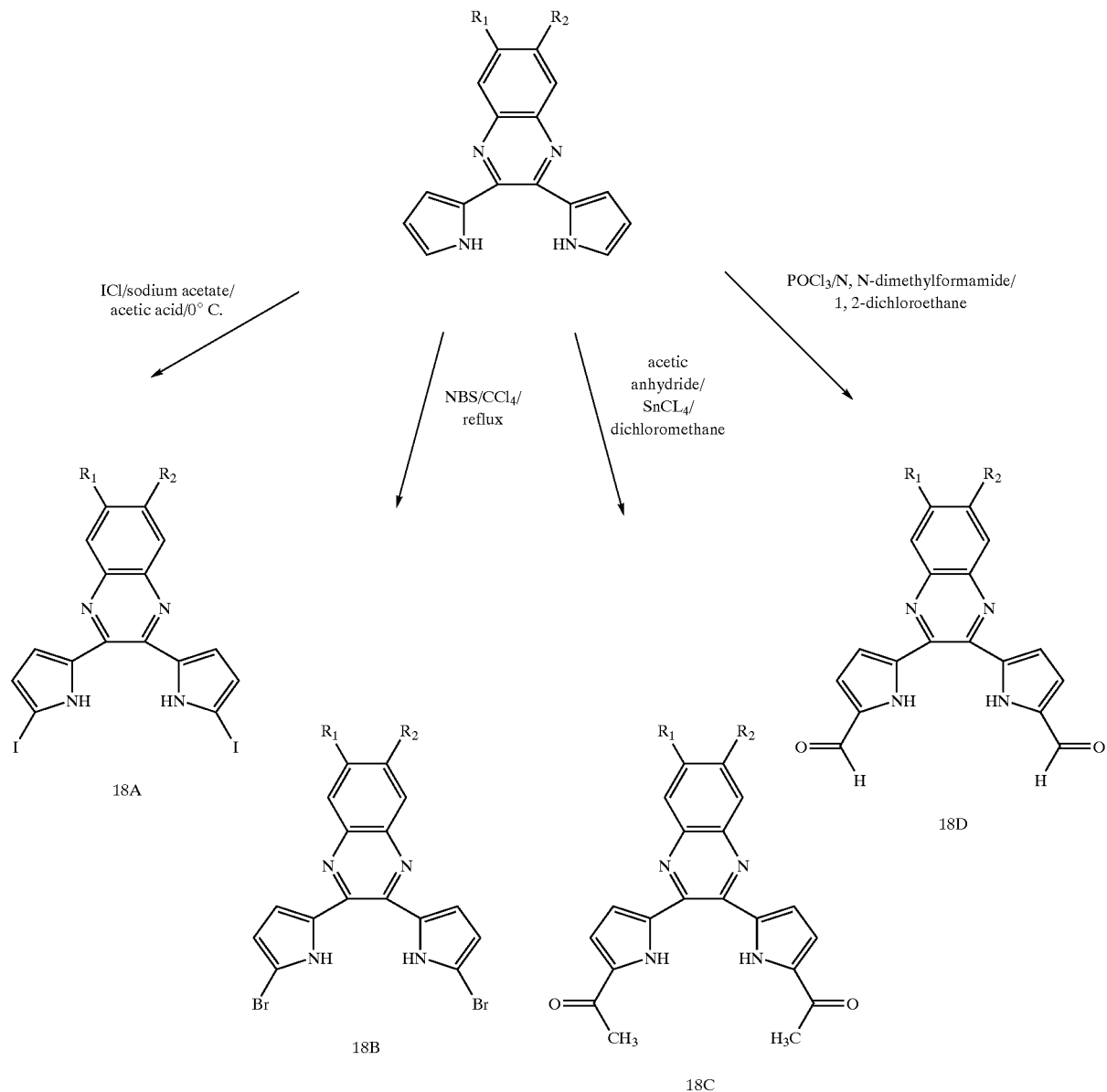

One of skill in the art will further recognize that the diiodo or the dibromo compounds may be modified through known synthetic means to generate a range of α-substituted compounds as exemplified by structures 19.

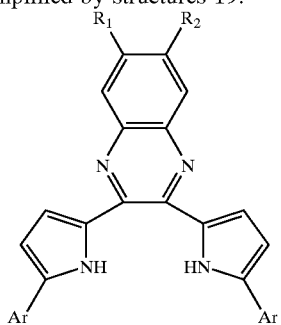

19

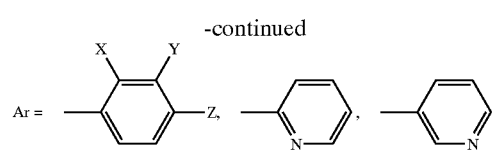

X=CHO, Y=Z=H
X=Z=H, Y=CHO
X=Y=H, Z=CHO
X=NO$_2$, Y=Z=H
X=Z=H, Y=NO$_2$
X=Y=H, ZNO$_2$
X=NH$_2$, Y=Z=H
X=Z=H, Y=NH$_2$
X=Y=H, Z=NH$_2$

Methods are also available for the synthesis of a TMS derivative as shown below:

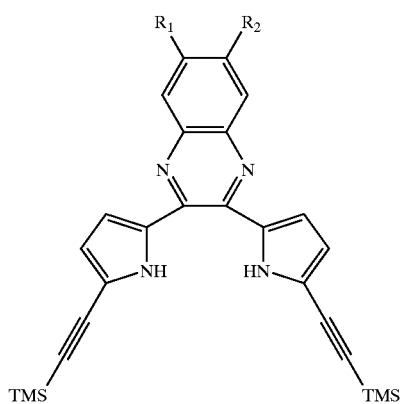

Removal of the TMS group and subsequent reaction with a metal salt, as described previously, will afford metal linked systems.

EXAMPLE 36

The Starting Pyrrole Unit as a Source of Variation

It will be apparent to one of skill in the art that many pyrrolylquinoxalines may be obtained within the context of the present invention. For example, as shown below, various substituents may be introduced on the starting pyrrole to generate a series of diones. These diones are then used in the synthesis of pyrrole-aryls to effect desired properties, such as a particular anion specificity, or increased solubility in a specific solvent. Accordingly it is contemplated that variety of approaches may be employed, in accordance with the present invention, to prepare an array of diones with a wide variety of substituents as represented in Scheme 5 below.

Scheme 5

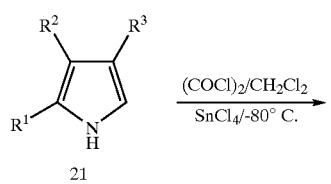

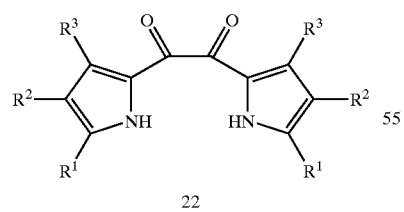

$R_1=CO_2CH_2CH_3$, $R_2=CH_3$, $R_3=CH_3$
$R_1=CO_2CH_2CH_3$, $R_2=CH_2CH_3$, $R_3=CH_2CH_3$
$R_1=CH_3$, $R_2=COCH_3$, $R_3=CH_3$
$R_1=CH_3$, $R_2=CO(CH_2)_nCH_3$, $R_3=CH_3$
$R_1=H$, $R_2=CH_3$, $R_3=CH_3$
$R_1=H$, $R_2=CH_2CH_3$, $R_3=CH_2CH_3$
$R_1H$, $R_2=R_3=CH_2(CH_2)_nCH_2$
n=1–10

It is further envisioned that different combinations of polypyrroles, in particular bipyrroles and terpyrroles, may be employed in the reaction with oxalyl chloride to produce various dione analogues as represented below.

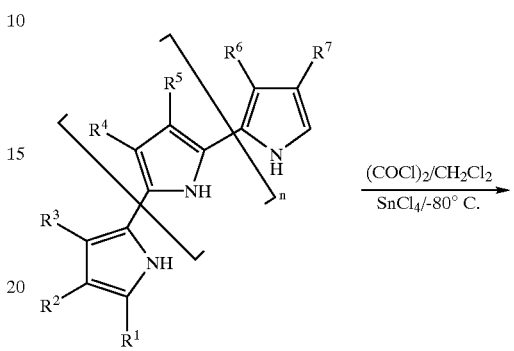

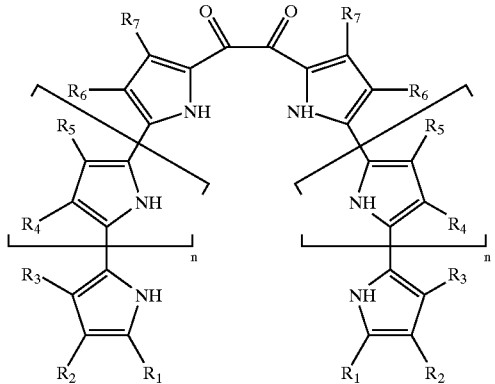

$R_1$ and $R_7$ are as described previously, n=1–10 with n=0, $R_1$–$R_7$=H preferred

EXAMPLE 37

Incorporation into Macrocycles

It is contemplated that the remaining α-free position on the pyrrole rings may react under a variety of conditions as shown below, to provide a number of novel compounds with a pyrrole-aryl and a macrocyclic component. These macrocycles may be used in fields such as anion binding (26), cation binding (28, 31, 32) and in optical devices (26, 28, 31, 32) and molecular wires (28, 31, 32).

In the following examples, $R_1$–$R_4$ are as previously described, n=0–10 with the preferred compound(s) as indicated within the synthetic scheme.

Scheme 7A
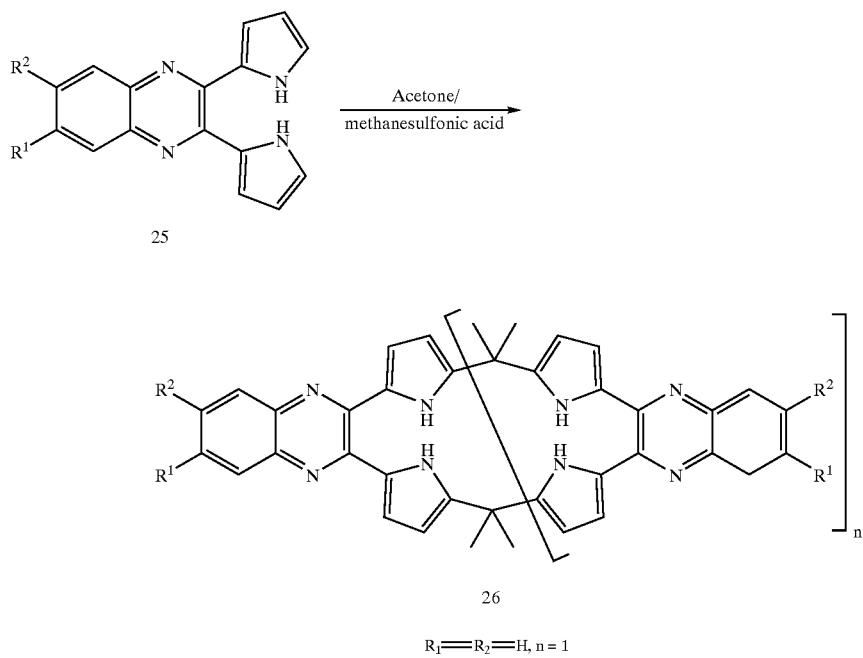
Scheme 7B
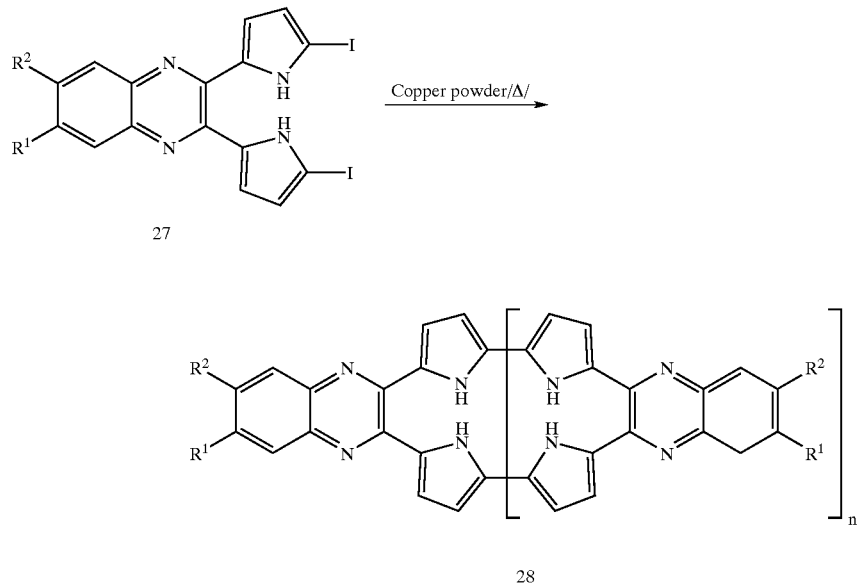
Scheme 7C
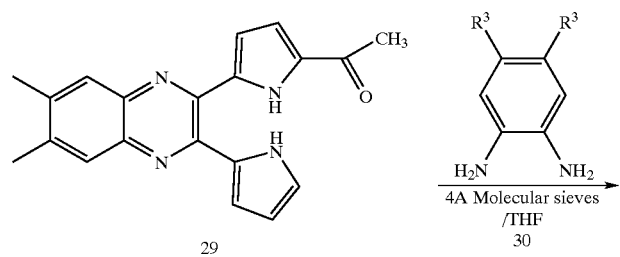

-continued

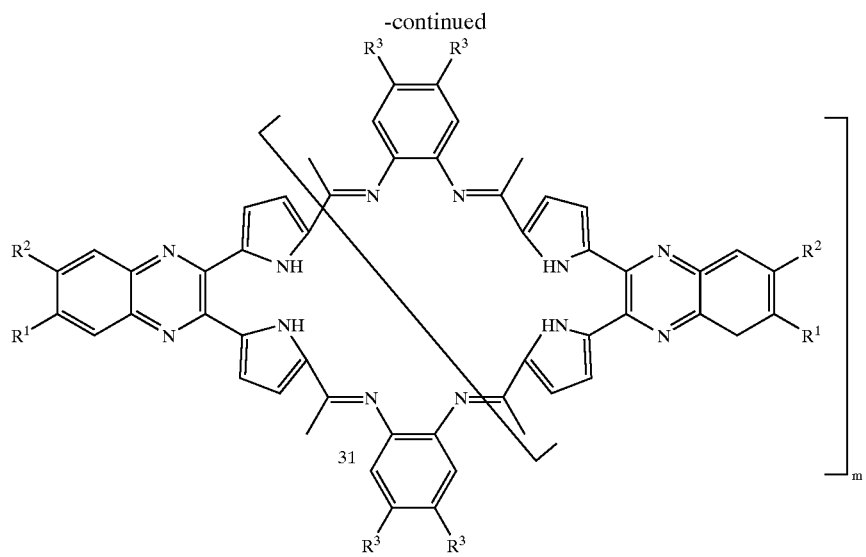

31

$R_1\!=\!R_2\!=\!R_3\!=\!H, n = 1$

Scheme 7D

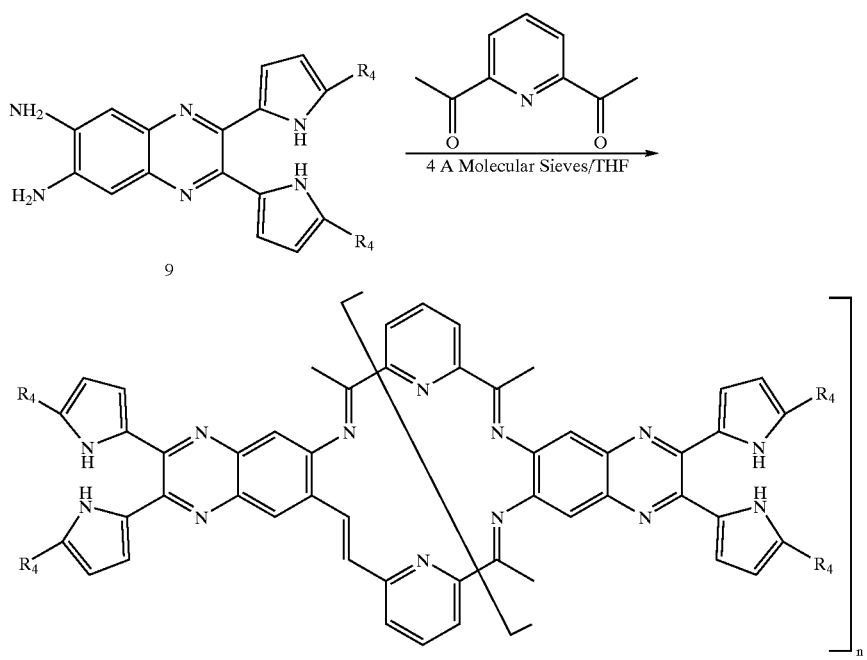

32 n = 1, 2, 3, etc.

$R_4$=H, n=1

It should again be stressed that although not shown above, all of the reaction schemes can be applied to analogues having widely substituted pyrrole rings. The pyrroles may be substituted both α and β, or in both ways to the pyrrole nitrogen atoms. The above reaction schemes are not intended to be limited to unsubstituted pyrroles or to the substitutions shown.

EXAMPLE 38

Alternate Heterocycles in the Starting Diketone

It is contemplated that alternate heterocyclic diones may be used in a condensation reaction with aryl 1,2-diamines, as outlined in previous examples, to produce 2,3-heteroaryl quinoxaline analogues. It is believed that these compounds will act as effective sensors for a variety of cations or neutrals. Compounds 33–38 below represent some proposed alternative diones contemplated for use in accordance with the present invention.

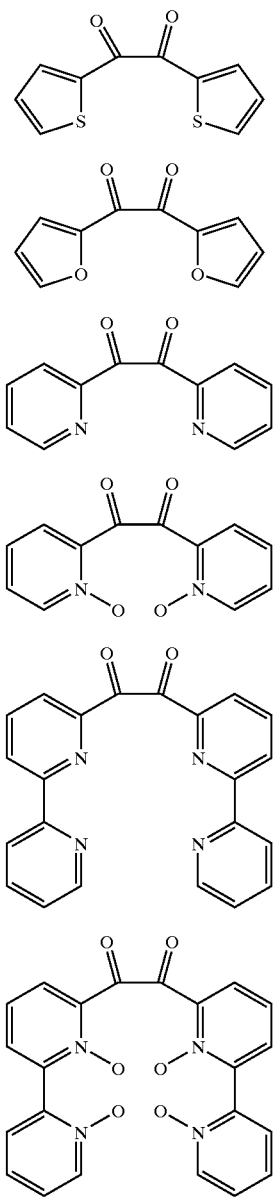

EXAMPLE 39

Dianions as Ligands

The pyrrole-aryls of the present invention may be used as sensors for anions, cations or neutral molecules provided the compound is of the appropriate charge of polarization. For instance, pyrrole-aryls of the present invention are contemplated for use as metal cation chelants by removing protons from the pyrrolic nitrogens as shown below.

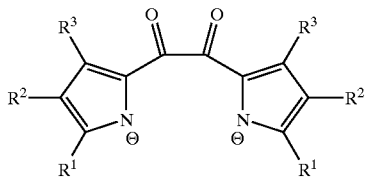

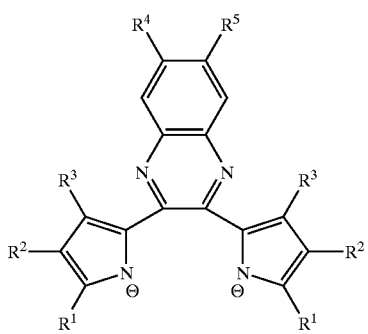

EXAMPLE 40

Pyrrole-Aryls As Anion Sensing Agents

The compounds of the present invention are used as anion sensors in a variety of applications including, chromatography, anion quantification, ion-selective electrodes and fiber-optics. A preferred example for use of the present compounds is for selective anion sensing, in particular fluoride sensing. Fluoride sensing has largely been complicated by competition from other biologically common species such as hydroxide, chloride and phosphate. The ability to sense fluoride is important for the analysis of drinking water, as well as ground water, in biological systems such as teeth and bones and in certain disease states such as fluorosis. In vitro sensing for fluoride is also important, for example to determine the amount of damaging fluorocarbons in the atmosphere and even the presence of fluorinated phosphates which can be used as chemical weapons due to their toxicity when ingested. The compounds of the present invention provide a distinct advantage over other sensors due to the selectivity for fluoride ion as demonstrated in Examples 7–9 and the dramatic color change produced upon binding. This makes the compounds particularly amenable for use in paper based sensing such as litmus paper, solid support sensing and as a coating on either fiber optic wires or electrodes. Selective sensing and separation are also contemplated using chromatographic methods. For example the present compounds may be coupled to a solid support and used to separate various anions from each other and from other species in the mixture. In certain circumstances a desired anion may even be collected as the system is entirely reversible based on the environment. Washing under appropriate conditions completely removes fluoride anion and returns the molecule to its original state.

It will also be apparent to one of skill in the art that many derivatives and analogues may be obtained within the context of the disclosed methods and compounds.

Once a range of pyrrole-aryl or alternate heterocyclic analogues have been generated, as described herein in the foregoing detailed examples, the specificity, kinetics and thermodynamics of anion binding under a range of conditions and with an array of different anions may be determined. The structure and function of the most promising compounds may then be optimized so that they bind the desired anion under the appropriate conditions, solvent, temperature, affinity pH etc., to function as an efficient sensor.

EXAMPLE 41

Synthesis of Water Soluble Pyrrole-Aryl Analogues

It is contemplated that the addition of charged groups and/or polar groups such as glycols or polyglycols to the 2,3-dipyrrylquinoxaline core will impart solubility in aqueous solutions. The synthesis of such a compound is outlined in the scheme below. The compound is that of 5 from Example 1.

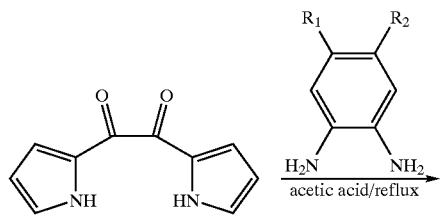

$R_1 = R_2 = O(CH_2CH_2O)_nCH_3$
n = 1–10, n = 3 preferred

It is further contemplated that the addition of further pyrroles to the quinoxaline subunit will result in the increase of solubility in aqueous solutions. The synthesis of such compounds is illustrated in the following schemes.

It is expected that these compounds will serve as sensors and therapeutic agents in aqueous solutions as described in the next example.

Scheme 8A

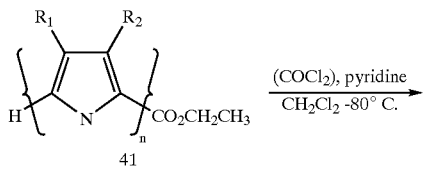

41

—continued

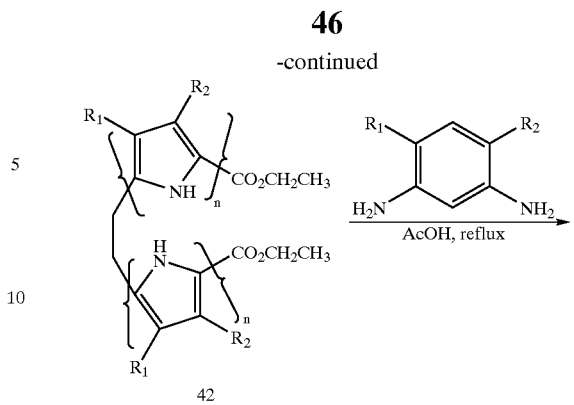

42

$R_1, R_2 = H$ or $NO_2$
$R_1 = R_2 = NO_2$
$R_1 = R_2 = X[(CH_2)_2O]_2CH_3$
with X = O, $CH_2$ or absent
$R_1 = H, R_2 = NHCO_9CH_2CO_2H$

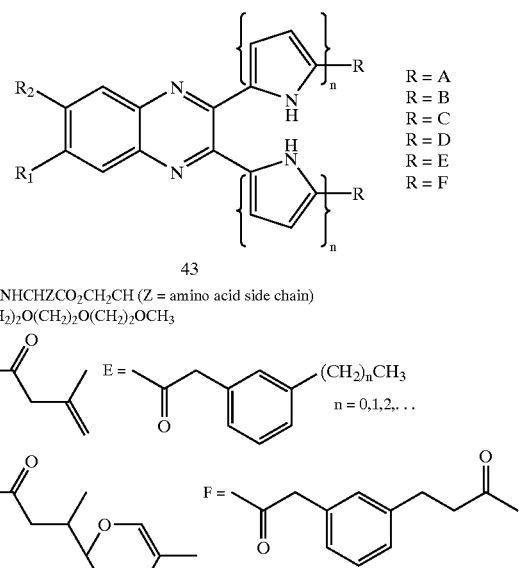

43

A = CONHCHZCO$_2$CH$_2$CH (Z = amino acid side chain)
B = $(CH_2)_2O(CH_2)_2O(CH_2)_2OCH_3$
C = [structure]
D = [structure]
E = [structure with $(CH_2)_nCH_3$, n = 0,1,2,...]
F = [structure]

Scheme 8B

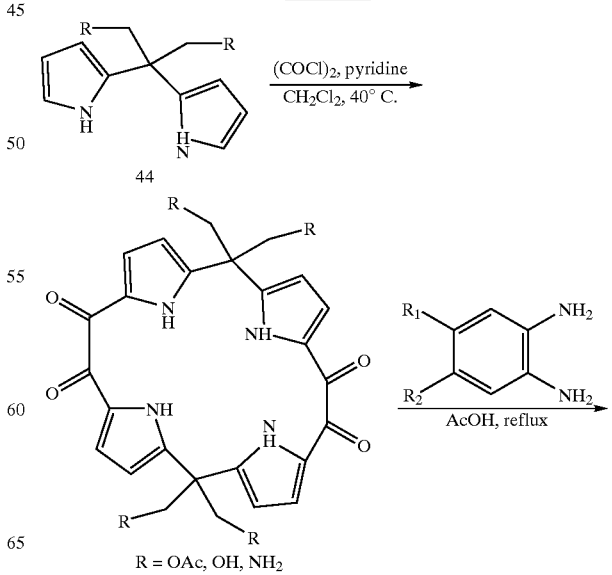

R = OAc, OH, NH$_2$

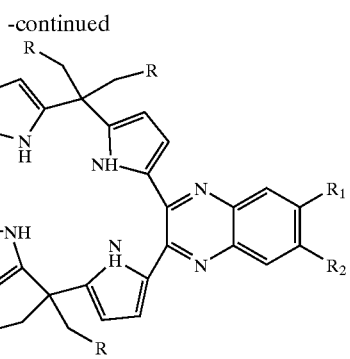

R₁ = R₂ = H
R₁ = R₂ = OCH₃
R₁ = R₂ = NO₂
R₁ = R₂ = CH₂((CH₂)₂O)₂CH₃
R₁ = H, R₂ = NHCO₂(CH₂)CO₂H

46

Scheme 8C

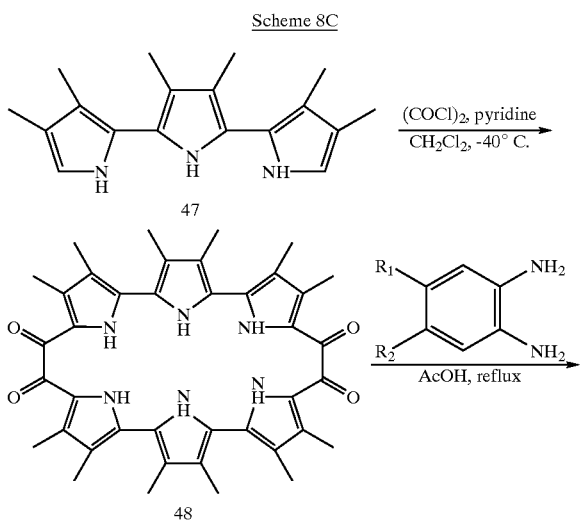

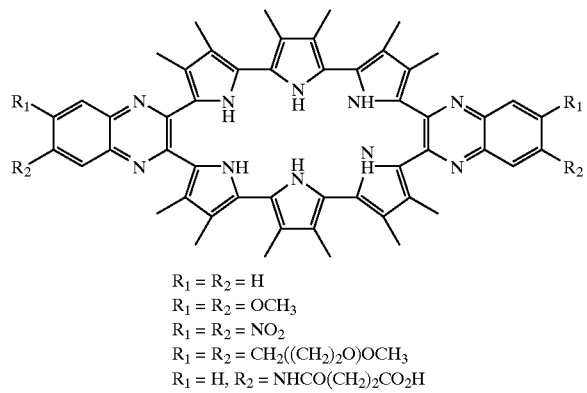

R₁ = R₂ = H
R₁ = R₂ = OCH₃
R₁ = R₂ = NO₂
R₁ = R₂ = CH₂((CH₂)₂O)OCH₃
R₁ = H, R₂ = NHCO(CH₂)₂CO₂H

EXAMPLE 42

Anion Binding Compounds as Therapeutic Agents

The compounds of the present invention, in particular those compounds with increased solubility in aqueous solutions are contemplated to be of use as in vivo anion sensors, for example blood samples, and as therapeutic agents to bind excess anion in certain disease states such as fluorosis.

To develop pyrrole-aryl compounds of the present invention for use as therapeutic agents, in vitro tests will be first conducted to determine the efficiency of binding, retention and selectivity in aqueous solutions. These will follow similar protocols as previously described for screening in organic solvents.

Following such in vitro tests, the binding activity of promising compounds will be followed up, in for example biological fluids such as blood, and then in in vivo animal studies. These studies will be conducted according to the standard practice for such animal trials, the execution of which will be ell known to one of skill in the art.

During the animal trials, the compounds may be further modified if required. They may be modified to increase solubility or to overcome in vivo degradation. Alternatively, if such problems occur, the compounds may be enveloped within a bio-compatible liposome and then administered intravenously.

Toxicity studies will also be carried out at this stage. The methods for determining both acute and chronic toxicity will be well known to one of skill in the art. Toxicity can be investigated in relation to solubility, net charge at physiological pH and changes in substituents.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

EXAMPLE 43

Sensing Compound Immobilized on a Solid Support

The usefulness of the pyrrole-aryl compounds as sensing agents when bound to solid supports was demonstrated by visual color change in the presence of tetrabutylammonium fluoride. 2,3-Dipyrrol-2'-yl-6-carboxyquinoxaline (preparation is described in Example 19) was immobilized on a polystyrene beads functionalized with polyethylene glycol groups that terminate in an amine. The quinoxaline is linked to TG-amino resin through an amide bond through a condensation reaction. An acetyl derivatized bead was used a blank.

The presence of fluoride ion was signaled by a dramatic visual color change from yellow to red for the 2,3-dipyrrol-2'-yl-6-carboxyquinoxaline-fuctionalized bead. The blank bead was initially colorless and remained so upon addition of fluoride ion.

REFERENCES

The following references, to the extent that they provide exemplary procedural or other details supplementary to those set forth herein, are specifically incorporated herein by reference.

Gale et al. Chem. Commun. 1998, 1–8.
Dietrich, B.; Hosseini, M. W. in Supramolecular Chemistry of Anions; Bianchi, A., Bowman-James, K. and Garcia-España, E., Ed.; Wiley-VCH: New York, 1997, pp 45–62.

Schmidtchen, F. P. Nachr. Chem, Tech. Lab. 1988, 36, 8–17.
K. L. Kirk Biochemistry of the Halogens and Inorganic HalidesPlenum Press: New York, 1991, p 58.
B. L. Riggs Bone and Mineral Research, Annual 2 Elsevier: Amsterdam, 1984, pp 366–393.
M. Kleerekoper Endocrinol. Metab. Clin. North Am. 1998, 27, 441–452.
A. Wiseman Handbook of Experimental Pharmacology XX/2.; Part. 2, Springer-Verlag: Berlin, 1970, pp 48–97.
Sessler, J. L.; Andrievsky, A.; Genge, J. W. in Advances in Supramolecular Chemistry; Lehn, J. M., Ed.; JAI Press Inc., 1997; Vol. 4, pp 97–142.
Gale, P. A.; Sessler, J. L.; Král, V. K.; Lynch, V. M. J. Am. Chem. Soc. 1996, 118, 5140–5141.
Sessler, J. L.; Gale, P. A.; Genge, J. W. Chem. Eur. J. 1998, 4, 1095–1099.
Dietrich, B.; Hosseini, M. W.; Lehn, J. M.; Sessions, R. B. J. Am. Chem. Soc. 1981, 103, 1282–1283.
Hosseini, M. W.; Lehn, J. M. Helvetica Chimica Acta 1988, 71, 749–756.
Dietrich, B.; Fyles, D. L.; Fyles, T. M.; Lehn, J. -M. Helvetica Chimica Acta 1979, 62, 2763–2787.
Metzger, A.; Lynch, V. M.; Anslyn, E. V. Angew. Chem. Int. Ed. Engl. 1997, 36, 862–865.
Oddo, B. Gazz. Chim. Ital. 1911, 41, 248–255.
Behr, D.; Brandänge, S.; Lindström, B. Acta Chem. Scand. 1973, 27, 2411–2414.
Sessler, J. L.; Mody, T. D.; Ramasamy, R.; Sherry, A. D. New J. Chem. 1992, 16, 541–544.
Cheeseman, G. W. H. 1962, J. Chem. Soc., 1170–1176.

What is claimed is:

1. A pyrrole-aryl compound of the general formula:

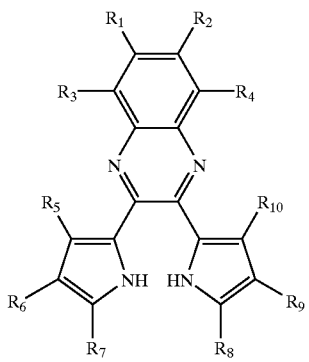

wherein $R_1$–$R_{10}$, individually at each occurrence, are the same or different and are selected from the group consisting of hydrogen, alkyl, hydroxyalkyl, glycolyl, polyglycol ether, amino, nitro, halo, cyano, aryl, heteroaryl, thio, thioalkyl, amido, ester, acyl, aldo, and carboxy;

wherein polyglycol ether is $O(CH_2CH_2O)_nCH_3$ and where n=1–10, wherein aryl is selected from the group consisting of phenyl and,
 a radical having 2–10 aromatic rings of carbon only, the individual rings being of 5–7 carbon atoms;

wherein heteroaryl is selected from the group consisting of
 one 5 or 6 membered aromatic ring, said ring containing at least one carbon atom and,
 a radical having 2–10 aromatic rings, said rings each containing 5 or 6 members and each ring having at least one carbon atom;

wherein ester is $R_aCOOR_b$ wherein $R_a$ and $R_b$ are alkyl and may consist of up to twenty carbon atoms and further wherein either $R_a$ or $R_b$ may be directly attached to the pyrrole aryl, wherein acyl is $R_aCOR_b$ wherein $R_a$ is alkyl and may consist of up to twenty carbon atoms, and wherein $R_b$ may consist of up to twenty atoms and further wherein either $R_a$ or $R_b$ may be directly attached to the pyrrole aryl, wherein carboxy is $R_aCOOH$ wherein $R_a$ is alkyl and may consist of up to twenty carbon atoms;

and salts thereof, provided, however, that $R_1$–$R_{10}$ cannot all be hydrogen.

2. The compound of claim 1, wherein $R_1$=$R_2$=$OCH_3$.
3. The compound of claim 1, wherein $R_1$=$R_2$=$NO_2$.
4. The compound of claim 1, wherein $R_1$=$R_2$=$CH_3$.
5. The compound of claim 1, wherein $R_1$=$R_2$=$O(CH_2CH_2O)_3CH_3$.
6. The compound of claim 1, wherein $R_1$=$R_2$=$O(CH_2)_nCH_3$, and wherein n is 0–20.
7. The compound of claim 1, wherein $R_1$=H, $R_2$=$NO_2$.
8. The compound of claim 1, wherein $R_1$=$NH_2$, $R_2$=$NO_2$.
9. The compound of claim 1, wherein $R_1$=$NH_2$, $R_2$=$NH_2$.
10. A compound selected from the group consisting of:

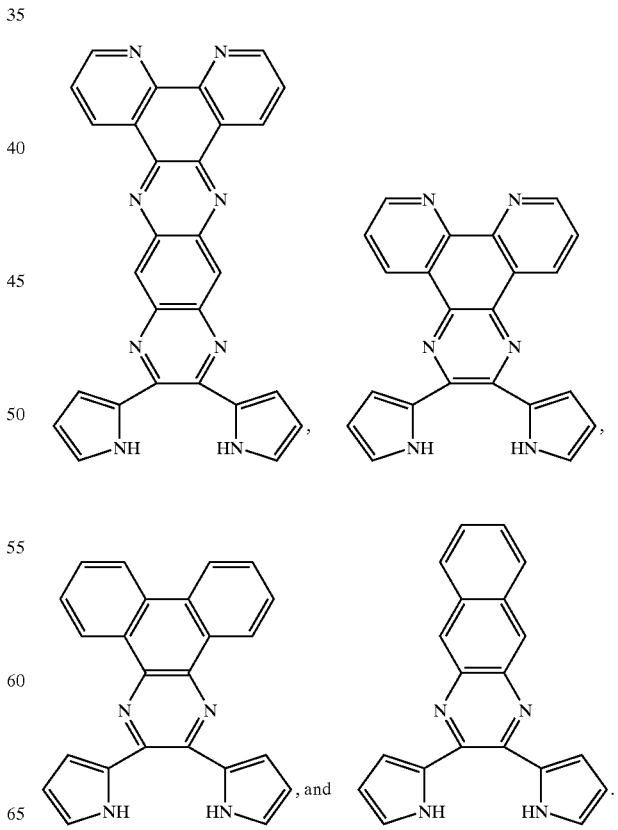

11. A compound of the general formula:

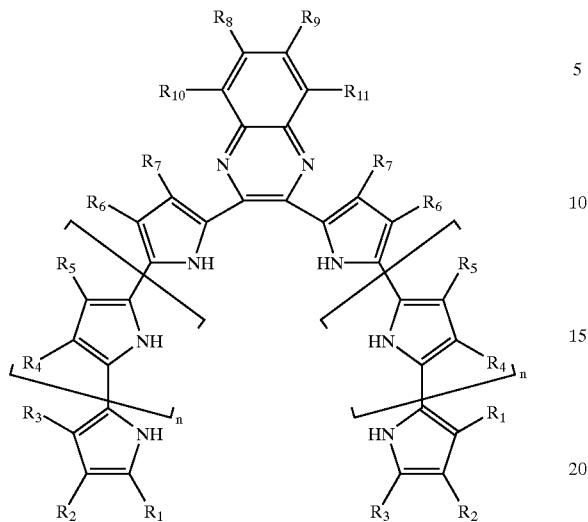

wherein $R_1-R_{11}$, individually at each occurrence, are the same or different and are selected from the group consisting of hydrogen, alkyl, hydroxyalkyl, glycolyl, polyglycol ether, amino, nitro, halo, cyano, aryl, heteroaryl, thio, thioalkyl, amido, ester, acyl, aldo, and carboxy;

wherein polyglycol ether is $O(CH_2CH_2O)_mCH_3$ and where m=1–10, wherein aryl is selected from the group consisting of phenyl and,
   a radical having 2–10 aromatic rings of carbon only, the individual rings being of 5–7 carbon atoms;

wherein heteroaryl is selected from the group consisting of
   one 5 or 6 membered aromatic ring, said ring containing at least one carbon atom and,
   a radical having 2–10 aromatic rings, said rings each containing 5 or 6 members and each ring having at least one carbon atom;

wherein ester is $R_aCOOR_b$ wherein $R_a$ and $R_b$ are alkyl and may consist of up to twenty carbon atoms and further wherein either $R_a$ or $R_b$ may be directly attached to rings of the compound, wherein acyl is $R_aCOR_b$ wherein $R_a$ is alkyl and may consist of up to twenty carbon atoms, and wherein $R_b$ may consist of up to twenty atoms and further wherein either $R_a$ or $R_b$ may be directly attached to rings of the compound, wherein carboxy is $R_aCOOH$ wherein $R_a$ is alkyl and may consist of up to twenty carbon atoms;

and n=0–10, and further wherein each of $R_1-R_7$ on either side of the axis of the quinoxaline bridge may be the same or different from the corresponding $R_1-R_7$ on the opposite side of the quinoxaline bridge and further wherein each $R_4$ and $R_5$ of the n subunits of pyrrole may be the same or different from corresponding $R_4$ and $R_5$ of any other subunits of pyrrole;

and salts thereof.

12. The compound of claim 11 wherein n=1.

13. The compound of claim 11 wherein n=2.

14. A pyrrole-aryl compound of the general structure:

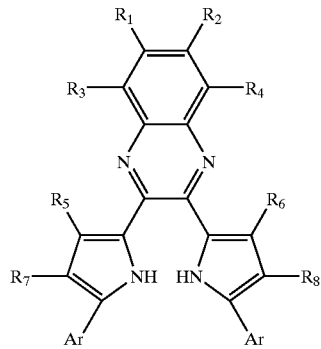

wherein $R_1-R_8$, individually at each occurrence, are the same or different and are selected from the group consisting of hydrogen, alkyl, hydroxyalkyl, glycolyl, polyglycol ether, amino, nitro, halo, cyano, aryl, heteroaryl, thio, thioalkyl, amido, ester, acyl, aldo, and carboxy;

wherein polyglycol ether is $O(CH_2CH_2O)_nCH_3$ and where n=1–10, wherein aryl is selected from the group consisting of phenyl and,
   a radical having 2–10 aromatic rings of carbon only, the individual rings being of 5–7 carbon atoms;

wherein heteroaryl is selected from the group consisting of
   one 5 or 6 membered aromatic ring, said ring containing at least one carbon atom and,
   a radical having 2–10 aromatic rings, said rings each containing 5 or 6 members and each ring having at least one carbon atom;

wherein ester is $R_aCOOR_b$ wherein $R_a$ and $R_b$ are alkyl and may consist of up to twenty carbon atoms and further wherein either $R_a$ or $R_b$ may be directly attached to the pyrrole aryl, wherein acyl is $R_aCOR_b$ wherein $R_a$ is alkyl and may consist of up to twenty carbon atoms, and wherein $R_b$ may consist of up to twenty atoms and further wherein either $R_a$ or $R_b$ may be directly attached to the pyrrole aryl, wherein carboxy is $R_aCOOH$ wherein $R_a$ is alkyl and may consist of up to twenty carbon atoms;

and further wherein Ar is selected from the group consisting of:

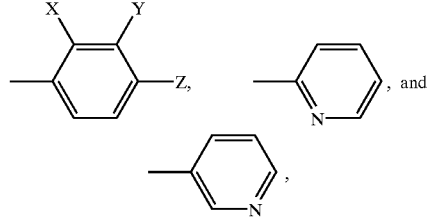

and further wherein X, Y, and Z are selected from the group consisting of hydrogen, aldehyde, nitro, and amino;

and salts thereof.

15. A pyrrole-quinoxaline compound of the general structure:

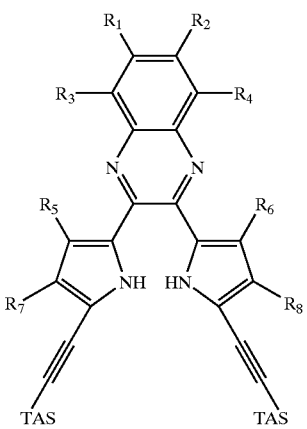

wherein $R_1$–$R_8$, individually at each occurrence, are the same or different and are selected from the group consisting of hydrogen, alkyl, hydroxyalkyl, glycolyl, polyglycol ether, amino, nitro, halo, cyano, aryl, heteroaryl, thio, thioalkyl, amido, ester, acyl, aldo, and carboxy;

wherein polyglycol ether is $O(CH_2CH_2O)_nCH_3$ and where n=1–10, wherein aryl is selected from the group consisting of
phenyl and,
a radical having 2–10 aromatic rings of carbon only, the individual rings being of 5–7 carbon atoms;

wherein heteroaryl is selected from the group consisting of
one 5 or 6 membered aromatic ring, said ring containing at least one carbon atom and,
a radical having 2–10 aromatic rings, said rings each containing 5 or 6 members and each ring having at least one carbon atom;

wherein ester is $R_aCOOR_b$ wherein $R_a$ and $R_b$ are alkyl and may consist of up to twenty carbon atoms and further wherein either $R_a$ or $R_b$ may be directly attached to the pyrrole-quinoxaline, wherein acyl is $R_aCOR_b$ wherein $R_a$ is alkyl and may consist of up to twenty carbon atoms, and wherein $R_b$ may consist of up to twenty atoms and fuirther wherein either $R_a$ or $R_b$ may be directly attached to the pyrrole-quinoxaline, wherein carboxy is $R_aCOOH$ wherein $R_a$ is alkyl and may consist of up to twenty carbon atoms;

and wherein TAS is a trialkylylsilyl group;

and salts thereof.

16. A pyrrole-aryl compound of the general formula:

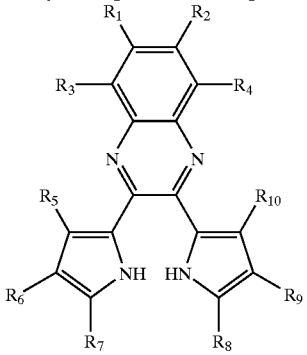

wherein $R_1$ and $R_2$ form part of a cyclic group said cyclic group selected from the group consisting of aryl or heteroaryl wherein aryl is selected from the group consisting of
phenyl and,
a radical having 2–10 aromatic rings of carbon only, the individual rings being of 5–7 carbon atoms;

and wherein heteroaryl is selected from the group consisting of
one 5 or 6 membered aromatic ring, said ring containing at least one carbon atom and,
a radical having 2–10 aromatic rings, said rings each containing 5 or 6 members and each ring having at least one carbon atom;

and further wherein $R_3$–$R_{10}$, individually at each occurrence, are the same or different and are selected from the group consisting hydrogen, alkyl, hydroxyalkyl, glycolyl, polyglycol ether, amino, nitro, halo, cyano, aryl, heteroaryl, thio, thioalkyl, amido, ester, acyl, aldo, and carboxy;

wherein polyglycol ether is $O(CH_2CH_2O)_nCH_3$ and where n=1–10, wherein aryl is selected from the group consisting of
phenyl and,
a radical having 2–10 aromatic rings of carbon only, the individual rings being of 5–7 carbon atoms;

wherein heteroaryl is selected from the group consisting of
one 5 or 6 membered aromatic ring, said ring containing at least one carbon atom and,
a radical having 2–10 aromatic rings, said rings each containing 5 or 6 members and each ring having at least one carbon atom;

wherein ester is $R_aCOOR_b$ wherein $R_a$ and $R_b$ are alkyl and may consist of up to twenty carbon atoms and further wherein either $R_a$ or $R_b$ may be directly attached to the pyrrole-aryl, wherein acyl is $R_aCOR_b$ wherein $R_a$ is alkyl and may consist of up to twenty carbon atoms, and wherein $R_b$ may consist of up to twenty atoms and further wherein either $R_a$ or $R_b$ may be directly attached to the pyrrole-aryl, wherein carboxy is $R_aCOOH$ wherein $R_a$ is alkyl and may consist of up to twenty carbon atoms;

and salts thereof, provided, however, that $R_3$–$R_{10}$ cannot all be hydrogen.

17. The pyrrole-aryl compound of claim 16 wherein polyglycol ether is $O(CH_2CH_2O)_nCH_3$ and where n=1–5.

18. The pyrrole-aryl compound of claim 1 wherein polyglycol ether is $O(CH_2CH_2O)_nCH_3$ and where n=1–5.

19. The compound of claim 11 wherein polyglycol ether is $O(CH_2CH_2O)_mCH_3$ and where m=1–5.

20. The pyrrole-aryl compound of claim 14 wherein polyglycol ether is $O(CH_2CH_2O)_nCH_3$ and where n=1–5.

21. The pyrrole-quinoxaline compound of claim 15 wherein polyglycol ether is $O(CH_2CH_2O)_nCH_3$ and where n=1–5.

22. The compound of any of claim 1, 10, 11, 14, 15, or 16 existing as a salt of one or more counterions selected from the group consisting of:
Group IA metals, Group IIA metals, ammonium, alkylammonium, and any combination thereof;
wherein one or more of the pyrrole nitrogens posses formal negative charge.

* * * * *

UNITED STATES PATENT AND TRADEMARK OFFICE
CERTIFICATE OF CORRECTION

PATENT NO. : 6,482,949 B1
DATED : November 19, 2002
INVENTOR(S) : Jonathan Sessler et al.

It is certified that error appears in the above-identified patent and that said Letters Patent is hereby corrected as shown below:

<u>Title page,</u>
Item [54], "COLORMETRIC" should be -- COLORIMETRIC --

Signed and Sealed this

Twenty-ninth Day of April, 2003

JAMES E. ROGAN
*Director of the United States Patent and Trademark Office*

UNITED STATES PATENT AND TRADEMARK OFFICE
CERTIFICATE OF CORRECTION

PATENT NO.          : 6,482,949 B1
APPLICATION NO.     : 09/579040
DATED               : November 19, 2002
INVENTOR(S)         : Jonathan Sessler et al.

Page 1 of 1

It is certified that error appears in the above-identified patent and that said Letters Patent is hereby corrected as shown below:

Title page,
Item [54] and Column 1, line 1, "COLORMETRIC" should be
--COLORIMETRIC--.

In column 1, lines 6-11, delete
"The government owns rights in the present invention pursuant to National Institutes of Health (grant no. GM 58907 to Jonathon L. Sessler), the National Science Foundation (CHE-9725399 to Jonathan L. Sessler), the Texas ARP (grant 003658-102 to JLS) and a NIH Postdoctoral Fellowship to Christopher B. Black." and insert
--This invention was made with government support under Grant No. GM 58907 awarded by the National Institutes of Health, Grant No. CHE-9725399 awarded by the National Science Foundation, Grant No. 003658-102 awarded by the Texas ARP, and a Postdoctoral Fellowship awarded by the National Institutes of Health. The government has certain rights in the invention.-- therefor.

This certificate supersedes the Certificate of Correction issued April 29, 2003.

Signed and Sealed this

Seventh Day of April, 2009

JOHN DOLL
*Acting Director of the United States Patent and Trademark Office*

UNITED STATES PATENT AND TRADEMARK OFFICE
CERTIFICATE OF CORRECTION

Page 1 of 1

PATENT NO. : 6,482,949 B1
APPLICATION NO. : 09/579040
DATED : November 19, 2002
INVENTOR(S) : Jonathan Sessler et al.

It is certified that error appears in the above-identified patent and that said Letters Patent is hereby corrected as shown below:

In the Specification

Column 1, at line 6 replace the entire paragraph with the following paragraph:

This invention was made with government support under Grant no. CHE9725399 awarded by the National Science Foundation; Grant no. DK018650, R01 DK033577 and GM058907 awarded by the National Institutes of Health. The government has certain rights in the invention.

Signed and Sealed this
Twenty-first Day of April, 2015

Michelle K. Lee
*Director of the United States Patent and Trademark Office*